(12) United States Patent
Liu et al.

(10) Patent No.: US 11,434,510 B2
(45) Date of Patent: Sep. 6, 2022

(54) LONG CHAIN DIBASIC ACID WITH LOW CONTENT OF LONG CHAIN DIBASIC ACID IMPURITY OF SHORTER CARBON-CHAIN AND PREPARATION METHOD THEREOF

(71) Applicants: Cathay Biotech Inc., Shanghai (CN); CIBT America Inc., Newark, DE (US)

(72) Inventors: Wenbo Liu, Shanghai (CN); Min Xu, Shanghai (CN); Chen Yang, Shanghai (CN); Howard Chou, Shanghai (CN); Xiucai Liu, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 562 days.

(21) Appl. No.: 16/503,309

(22) Filed: Jul. 3, 2019

(65) Prior Publication Data

US 2020/0010859 A1 Jan. 9, 2020

(51) Int. Cl.
| | |
|---|---|
| C12P 7/44 | (2006.01) |
| C12N 15/52 | (2006.01) |
| C12N 9/02 | (2006.01) |
| C12N 15/01 | (2006.01) |
| C12P 7/6409 | (2022.01) |

(52) U.S. Cl.
CPC .............. *C12P 7/44* (2013.01); *C12N 15/52* (2013.01); *C12Y 103/03006* (2013.01)

(58) Field of Classification Search
None
See application file for complete search history.

(56) References Cited

FOREIGN PATENT DOCUMENTS

| WO | WO 03/100013 | 12/2003 |
|---|---|---|
| WO | WO 2004/013336 | 2/2004 |
| WO | WO 2004/100504 | 11/2004 |

OTHER PUBLICATIONS

Extended European Search report for Application No. 19184879.5, dated Nov. 15, 2019, 18 pages.
Hara et al., "Repression of fatty-acyl-CoA oxidase-encoding gene expression is not necessarily a determinant of high-level production of dicarboxylic acids in industrial dicarboxylic-acid-producing Candida tropicalis", Appl Microbiol Biotechnol (2001) 56:478-485.
Okazaki et al., "Peroxisomal acyl-coenzyme A oxidase multigene family of the yeast *Candida tropicalis*; nucleotide sequence of a third gene and its protein product", Gene, 58 (1987) 37-44.
Okazaki et al., "Two acyl-coenzyme A oxidases in peroxisomes of the yeast *Candida tropicalis*: Primary structures deduced from genomic DNA sequence", Proc. Natl. Acad. Sci. USA, vol. 83, pp. 1232-1236, Mar. 1986 Biochemistry.
Picataggio et al., "Determination of *Candida tropicalis* Acyl Coenzyme A Oxidase Isozyme Function by Sequential Gene Disruption", Molecular and Cellular Biology, Sep. 1991, p. 4333-4339.
Smit et al., "α,ω-Dicarboxylic acid accumulation by acyl-CoA oxidase deficient mutants of *Yarrowia lipolytica*", Biotechnology Letters (2005) 27: 859-864.
Werner et al., "Biotechnological production of bio-based long-chain dicarboxylic acids with oleogenious yeasts", World J Microbiol (2017) 33:194.

*Primary Examiner* — Suzanne M Noakes
*Assistant Examiner* — Jae W Lee
(74) *Attorney, Agent, or Firm* — Adsero IP

(57) ABSTRACT

The present invention relates to a long-chain dibasic acid with low content of long-chain dibasic acid impurity of shorter carbon chain, to the preparation of a long-chain dibasic acid producing strain by directed evolution of POX gene and homologous recombination, and to the production of a long-chain dibasic acid with low content of long-chain dibasic acid impurity of shorter carbon chain by using the strain. The present invention also relates to a strain containing a mutated promoter, wherein, when a long-chain dibasic acid is produced by fermentation of this strain, the content of the acid impurity of shorter carbon chain in the fermentation product is significantly reduced.

3 Claims, 2 Drawing Sheets

Specification includes a Sequence Listing.

```
192  GTGATTTGGCACTTGACAGCGCGAGAGTGGTTAACACCTGGTTTCCCTCATTTGGGTTCT
526  GTGATTTGGCACTTGACAGCGCGAGAGTGGTTAACACCTGGTTTCCCTCATTTGGGTTCT
     ************************************************************

192  GACATTTGATAAGTTGAAAGAACAATGCAGAATTCACATGGCTAATTTGGCCTCGGTTCC
526  GACATTTGATAAGTTGAAAGAACAATGCAGAATTCACATGGCTAATTTGGCCTCGGTTCC
     ************************************************************

192  ACAACGCACTCAGCATTAAAAAAAAAATACGCAATGGCAGCTCGGTCGACGCAGCAGAAG
526  ACAACGCACTCAGCATTAAAAAAAAAATACGCAATGGCAGCTCGGTCGACGCAGCAGAAG
     ************************************************************

192  CGCCGACGTACCGTCGCGTTGCCCCGCCCATGCCTCGCCGACCCCTCCACCGCCATCGTT
526  CGCCGACGTACCGTCGCGTTGCCCCGCCCATGCCTCGCCGACCCCTCCACCGCCATCGTT
     ************************************************************

192  TGCCCATTGTTTGTGGTAGTGCGCCGTGACACAAAAACTTGTCCTGTCACATGCTGAAGT
526  TGCCCATTGTTTGTGGTAGTGCGCCGTGACACAAAAACTTGTCCTGTCACATGCTGAAGT
     ************************************************************

192  TACACCAACATAACTACTATGGGATTACGTAATCAAAAATTTCACAGTTTTAACAAAAAA
526  TACACCAACATAACTACTATGGGATTACGTAATCAAAAATTTCACAGTTTTAACAAAAAA
     ************************************************************

192  AAAATCATACAATCAACATTGGGACATCTTGCCCTCCCCCACAAAACTTGCTTCTGCATC
526  AAA-TCATACAATCAACATTGGGACATCTTGCCCTCCCCCACAAAACTTGCTTCTGCATC
     *** ********************************************************

192  AATCATATATAAACATCATGAAATAAGCCTAAACTCACTTCTTTTTTTTTCATCCTTCCT
526  AATCATATATAAACATCATGAAATAAGCCTAAACTCACTTCTTTTTTTTTCATCCTTCCT
     ************************************************************

192  ACTTCTTCTTTCATAGTAACTACTTTTTTTTTATTACCACACTTATTCATTCATACCACG
526  ACTTCTTCTTTCATAGTAACTACTTTTTTTTTATTACCACACTTATTCATTCATACCACG
     ************************************************************

192  CTATC
526  CTATC
     *****
```

Figure 2

LONG CHAIN DIBASIC ACID WITH LOW CONTENT OF LONG CHAIN DIBASIC ACID IMPURITY OF SHORTER CARBON-CHAIN AND PREPARATION METHOD THEREOF

CROSS-REFERENCE TO RELATED APPLICATIONS

This application claims priority to and the benefit of Chinese Patent Application No. 201810734151.8, filed on Jul. 6, 2018 and Chinese Patent Application No. 201810734262.9 filed on Jul. 6, 2018, and Chinese Patent Application No. 201910378102.X, filed on May 8, 2019, the disclosures of which are incorporated herein by reference in their entirety.

Sequence Statement Incorporated by reference herein in its entirety is the Sequence Listing entitled "NI2018TC411US_sequence_listing," created Jul. 6, 2018, size of 37 kilobytes.

TECHNICAL FIELD

The present invention relates to a long-chain dibasic acid with low content of long-chain dibasic acid impurity of shorter carbon-chain and a preparation method thereof. Specifically, the present invention relates to a long-chain dibasic acid with low content of long-chain dibasic acid impurity of shorter carbon-chain, and a method for preparing a long-chain dibasic acid producing strain by directed evolution of POX gene and homologous recombination, as well as a method for producing a long-chain dibasic acid with low content of long-chain dibasic acid impurity of shorter carbon-chain by using the strain through fermentation.

BACKGROUND ART

Long-chain dibasic acid (LCDA; also known as long-chain dicarboxylic acid or long-chain diacid) comprises a dibasic acid of the chemical formula $HOOC(CH_2)_nCOOH$, where $n \geq 7$. As important monomer raw material, long-chain dibasic acid is widely used in the synthesis of nylon, resins, hot melt adhesives, powder coatings, preservatives, perfumes, lubricants, plasticizers and the like.

For a long time, long-chain dibasic acid is synthesized from petroleum through conventional chemical synthesis pathways, for example, from butadiene by a multi-step oxidation process. However, the chemical synthesis method faces various challenges. Dibasic acid obtained by the chemical synthesis method is a mixture of long-chain dibasic acid and short-chain dibasic acid. Therefore, complex subsequent extraction and purification steps are required, which are huge obstacles for production process and production cost. Due to low pollution, environmental friendliness, and the ability to synthesize products that are difficult to be synthesized by chemical synthesis method, such as a long-chain dibasic acid having 12 or more carbon atoms, and high purity and other characteristics, the microbiological fermentation technique for the production of a long-chain dibasic acid has obvious advantages over traditional chemical synthesis method.

But using the microbiological fermentation method for producing a long-chain dibasic acid, there are residual impurities in the products sometimes and the reduction in the product purity affects the quality of the product significantly, which greatly affects its later application. In particular, the impurity which is characteristically similar to the long-chain dibasic acid not only generates technical challenges to the later extraction and purification, but also produces great negative effects on the production cost control. Therefore, to genetically modify a strain for producing a long-chain dibasic acid so as to reduce the content of certain impurity during the fermentation is important and valuable in industry to the dibasic acid production via biological synthesis.

Previously, the improvement of a dibasic acid producing strain was mostly achieved through conventional random mutagenesis or genetic engineering methods. Due to the characteristic of random mutagenesis, there is a high requirement for screening throughput, and a new round of mutagenesis screening is required for each changed trait, which has become an important limiting factor technically. The genetic engineering means can be used to perform targeted genetic modification of a strain, so as to obtain a better strain with higher yield. The microbiological fermentation method of a long-chain dibasic acid is mainly based on ω-oxidation of alkane, which can then be degraded by β-oxidation pathway. Previous studies have shown that the yield of a long-chain dibasic acid can be increased by means of enhancing the ω-oxidation pathway and inhibiting the β-oxidation pathway. Pictaggio et al. of Coginis company (Mol. Cell. Biol., 11(9), 4333-4339, 1991) reported that knocking out two alleles of each of POX4 and POX5 could effectively block the β-oxidation pathway to achieve 100% conversion rate of the substrate. Further overexpression of the genes of two key enzymes, P450 and oxidoreductase POX, of the rate-limiting step in the ω-oxidation pathway could effectively increase production. Xiaoqin Lai et al. (Chinese patent CN103992959B) reported that the introduction of one copy of the CYP52A14 gene into a dibasic acid-producing strain could also effectively increase the conversion rate and production efficiency of the dibasic acid. In addition, Zhu'an Cao et al from Tsinghua University (Biotechnol. J., 1, 68-74, 2006) found that knocking out a copy of the key gene CAT in the transportation of acetyl coenzyme A from peroxisome to mitochondria could partially block acetyl coenzyme A entering the citric acid cycle, and also effectively reduce the degradation of dibasic acids.

Error-prone PCR is the technique proposed by Leung et al. (Technique, 1, 11-15, 1989) to construct a gene library for directed studies. By changing PCR conditions, such as adjusting the concentration of four deoxyribonucleic acids in the reaction system, changing the concentration of $Mg^{2+}$, and using a low-fidelity DNA polymerase and the like, a base is mismatched so as to introduce a mutation. Too high or too low mutation rate will affect the effect of constructing mutant libraries. The ideal base mutation ratio is 1-3 per DNA fragment. Therefore, the beneficial mutations that contribute to further improvement of the strain productivity can be screened out through gene-directed genetic modification by using error-prone PCR to generate random mutation(s) in combination with homologous recombination.

In the past, most of the modifications to dibasic acid producing strains focused on random mutagenesis or overexpressing the genes in the upstream synthesis pathway or blocking the downstream β-oxidation pathway. There is no report or application regarding directed evolution of a gene in the metabolic pathway. There is a need in the art for a strain capable of significantly increasing the yield of a long-chain dibasic acid and significantly reducing the content of partial impurities and a preparation method thereof.

SUMMARY OF THE INVENTION

In the first aspect, the present invention relates to a long-chain dibasic acid with low content of long-chain dibasic acid impurity of shorter carbon-chain, wherein the content of the long-chain dibasic acid impurity of shorter carbon-chain is more than 0 and less than 500 ppm, preferably less than 400 ppm, preferably less than 300 ppm, preferably less than 250 ppm and more preferably less than 200 ppm, and wherein the number of carbon atoms in the long-chain dibasic acid impurity of shorter carbon-chain is less than the number of carbon atoms in the long-chain dibasic acid.

In some embodiments, the long-chain dibasic acid is selected from the group consisting of C9-C22 long-chain dibasic acids, preferably C9-C18 long-chain dibasic acids, and more preferably comprises one or more selected from the group consisting of C10 dibasic acid, C11 dibasic acid, C12 dibasic acid, C13 dibasic acid, C14 dibasic acid, C15 dibasic acid and C16 dibasic acid; and more preferably, the long-chain dibasic acid is at least one of C10 to C16 dibasic acids, or at least one of n-C10 to C16 dibasic acids, e.g. at least one selected from the group consisting of sebacic acid, undecanedioic acid, dodecanedioic acid, tridecanedioic acid, tetradecanedioic acid, pentadecanedioic acid and hexadecanedioic acid.

In some embodiments, when the long-chain dibasic acid is C12 dibasic acid such as dodecanedioic acid, the long-chain dibasic acid impurity of shorter carbon-chain is predominantly C10 long-chain dibasic acid, and the content of C10 long-chain dibasic acid impurity is less than 350 ppm, preferably less than 300 ppm, 290 ppm, 280 ppm, 270 ppm, 260 ppm, 250 ppm, 240 ppm, 230 ppm, 220 ppm, or 210 ppm or less.

In the second aspect, the present invention relates to a fermentation broth in a process of producing a long-chain dibasic acid by a microbiological fermentation method. The fermentation broth contains a long-chain dibasic acid impurity of shorter carbon-chain, and the mass ratio of the long-chain dibasic acid impurity of shorter carbon-chain is less than 1.5%, preferably less than 1.0%, less than 0.9%; wherein the mass ratio is the mass percentage of the long-chain dibasic acid impurity of shorter carbon-chain to the long-chain dibasic acid in the fermentation broth.

In some embodiments, when the long-chain dibasic acid is C12 dibasic acid such as dodecanedioic acid, the long-chain dibasic acid impurity of shorter carbon-chain is predominantly C10 long-chain dibasic acid.

In the third aspect, the present invention relates to a method for producing a long-chain dibasic acid according to the first aspect, comprising obtaining a long-chain dibasic acid producing microorganism strain containing a mutated POX gene, a homologous gene or a variant thereof by directed evolution of the POX gene in the long-chain dibasic acid synthesis pathway, culturing the strain to produce the long-chain dibasic acid by fermentation; optionally, further comprising isolating, extracting and/or purifying the long-chain dibasic acid from the culture product.

Relative to the Gen Bank Accession Number M12161 (e.g. set forth in SEQ ID NO: 24), taking first base upstream of the start codon ATG (e.g. the base "C" at position 456 of SEQ ID NO: 24) as −1, the mutated POX gene, homologous gene or variant thereof comprises the mutation −182_−191AAAAAAAAAA>AAAAAAAAA, e.g. the base mutation −182delA, in its promoter region; and the variant has at least 70% sequence identity with the mutated POX gene or the homologous gene.

In some embodiments, the sequence of the mutated POX gene is set forth in SEQ ID NO: 16 or a sequence having at least 70%, for example at least about 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95%, or 99.96% sequence identity thereto.

In some embodiments, the content of the long-chain dibasic acid impurity of shorter carbon-chain is decreased by at least 5%, preferably at least 10%, more preferably at least 20%, more preferably at least 40%, more preferably at least 50% or more, compared with the content of long-chain dibasic acid impurity of shorter carbon-chain produced by fermentation of a conventional microorganism (e.g. a non-mutant microorganism not containing the mutated POX gene according to the invention).

In some embodiments, when the long-chain dibasic acid is C12 dibasic acid such as dodecanedioic acid, the long-chain dibasic acid impurity of shorter carbon-chain is predominantly C10 long-chain dibasic acid.

In some embodiments, the microorganism is yeast, preferably selected from *Candida tropicalis* or *Candida sake.*

In some embodiments, obtaining a long-chain dibasic acid producing microorganism strain containing a mutated POX gene, a homologous gene or a variant thereof comprises the steps of:

1) preparing a fragment carrying a target gene (POX gene) having a mutation by error-prone PCR;

2) preparing fragments upstream and downstream of the target gene (POX gene) necessary for homologous recombination as templates for homologous recombination and a resistance maker gene, preferably the resistance maker gene is hygromycin B;

3) preparing a complete recombinant fragment by PCR overlap extension;

4) introducing the recombinant fragment into a strain by homologous recombination;

5) screening a positive strain by means of the resistance maker;

6) screening a strain that the content of the long-chain dibasic acid impurity of shorter carbon-chain is decreased; and 7) optionally, removing the resistance marker in the screened strain by further homologous recombination.

In the fourth aspect, the present invention relates to a mutated POX gene, a homologous gene or a variant thereof, relative to Genbank Accession Number M12161 (e.g. set forth in SEQ ID NO: 24), taking the first base upstream of the start codon ATG (e.g. the base "C" at position 456 in SEQ ID NO: 24) as −1, having mutation −182_−191AAAAAAAAAA>AAAAAAAAA, e.g. a base mutation −182delA, in its promoter region; and the variant has at least 70% sequence identity with the mutated POX gene or homologous gene thereof.

In some embodiments, the sequence of the mutated POX gene is set forth in SEQ ID NO: 27 or SEQ ID NO: 29 or has at least 70%, e.g. at least about 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95% or 99.96% sequence identity thereto.

In some embodiments, the sequence of the mutated POX gene is set forth in SEQ ID NO: 16 or has at least 70%, e.g. at least about 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95% or 99.96% sequence identity thereto.

In the fifth aspect, the present invention relates to a microorganism containing the mutated POX gene, homologous gene or variant thereof according to the fourth aspect of the invention, which, relative to a microorganism containing a non-mutated POX gene, homologous gene or variant thereof, produces a long chain dibasic acid with significantly decreased content of long-chain dibasic acid impurity of shorter carbon-chain, wherein the number of carbon atoms in the long-chain dibasic acid impurity of shorter carbon-chain is less than the number of carbon atoms in the long-chain dibasic acid.

Preferably, the microorganism is selected from the group consisting of *Corynebacterium, Geotrichum candidum, Candida, Pichia, Rhodotroula, Saccharomyces* and *Yarrowia*, more preferably the microorganism is yeast, and more preferably the microorganism is *Candida tropicalis* or *Candida sake*. In a particular embodiment, the microorganism is CCTCC M2011192 or CCTCC M203052.

In some embodiments, the long-chain dibasic acid is C9 to C22 long-chain dibasic acids, preferably C9 to C18 long-chain dibasic acids, more preferably comprises one or more selected from the group consisting of C10 dibasic acid, C11 dibasic acid, C12 dibasic acid, C13 dibasic acid, C14 dibasic acid, C15 dibasic acid and C16 dibasic acid. In some embodiments, the long-chain dibasic acid is at least one or more of C10 to C16 dibasic acids, or at least one or more of n-C10 to C16 dibasic acids, e.g. at least one selected from the group consisting of sebacic acid, undecanedioic acid, dodecanedioic acid, tridecanedioic acid, tetradecanedioic acid, pentadecanedioic acid and hexadecanedioic acid. The sebacic acid is n-C10 dibasic acid.

In the sixth aspect, the present invention relates to a method of producing a long-chain dibasic acid by using the microorganism according to the fifth aspect, comprising culturing the microorganism according to the fifth aspect, and optionally isolating and/or purifying the long-chain dibasic acid from the culture product.

In some embodiments, after the completion of the process of producing a long-chain dibasic acid by fermentation with the microorganism, the fermentation broth contains long-chain dibasic acid impurity of shorter carbon-chain, and the mass ratio of the long-chain dibasic acid impurity of shorter carbon-chain is below 1.50%, wherein the mass ratio is the mass percentage of the long-chain dibasic acid impurity of shorter carbon-chain to the long-chain dibasic acid in the fermentation broth.

In some embodiments, after the completion of the process of producing a long-chain dibasic acid by fermentation with the microorganism, the fermentation broth contains long-chain dibasic acid impurity of shorter carbon-chain, and compared with the fermentation using a conventional microorganism (e.g. a non-mutant microorganism not containing the mutated POX gene according to the invention), e.g. a fermentation using a non-mutant microorganism according to the invention, the content of the long-chain dibasic acid impurity of shorter carbon-chain is decreased by at least 5%.

In the seventh aspect, the present invention relates to a long chain dibasic acid obtained by the method according to the sixth aspect, wherein the long chain dibasic acid comprises long-chain dibasic acid impurity of shorter carbon-chain, and the content of the long-chain dibasic acid impurity of shorter carbon-chain is more than 0 and less than 500 ppm, preferably less than 400 ppm, preferably less than 300 ppm, preferably less than 250 ppm, and more preferably less than 200 ppm, and wherein the number of carbon atoms in the long-chain dibasic acid impurity of shorter carbon-chain is less than the number of carbon atoms in the long-chain dibasic acid.

In some embodiments, the long-chain dibasic acid is C9 to C22 long-chain dibasic acids, preferably C9 to C18 long-chain dibasic acids, more preferably comprises one or more selected from the group consisting of C10 dibasic acid, C11 dibasic acid, C12 dibasic acid, C13 dibasic acid, C14 dibasic acid, C15 dibasic acid and C16 dibasic acid. More preferably, the long-chain dibasic acid is at least one or more of C10 to C16 dibasic acids, or at least one or more of n-C10 to C16 dibasic acids, e.g. at least one selected from the group consisting of sebacic acid, undecanedioic acid, dodecanedioic acid, tridecanedioic acid, tetradecanedioic acid, pentadecanedioic acid and hexadecanedioic acid.

In some embodiments, the content of the long-chain dibasic acid impurity of shorter carbon-chain is less than 500 ppm. Preferably, when the long-chain dibasic acid is C12 dibasic acid such as dodecanedioic acid, the long-chain dibasic acid impurity of shorter carbon-chain is predominantly C10 long-chain dibasic acid such as sebacic acid, and the content of C10 long-chain dibasic acid impurity is less than 350 ppm, preferably less than 300 ppm, 290 ppm, 280 ppm, 270 ppm, 260 ppm, 250 ppm, 240 ppm, 230 ppm, 220 ppm, or 210 ppm or less.

In the eighth aspect, the present invention relates to a method for modifying a long-chain dibasic acid producing microorganism strain, comprising a step of direct-evolution of a key gene in the pathway of the long-chain dibasic acid synthesis, wherein, compared to the microorganism strain before modified, the modified long chain dibasic acid producing microorganism strain is capable of producing the long chain dibasic acid with substantially decreased content of the long-chain dibasic acid impurity of shorter carbon-chain, e.g. under the same conditions.

Preferably, the key gene in the pathway of the long-chain dibasic acid synthesis is POX gene.

Preferably, the microorganism is selected from the group consisting of *Corynebacterium, Geotrichum candidum, Candida, Pichia, Rhodotroula, Saccharomyces* and *Yarrowia*, more preferably the microorganism is yeast, and more preferably the microorganism is *Candida tropicalis* or *Candida sake*. In a particular embodiment, the microorganism is CCTCC M2011192 or CCTCC M203052.

Preferably, the long-chain dibasic acid is selected from C9 to C22 long-chain dibasic acids, preferably selected from C9 to C18 long-chain dibasic acids, more preferably comprises one or more selected from the group consisting of C10 dibasic acid, C11 dibasic acid, C12 dibasic acid, C13 dibasic acid, C14 dibasic acid, C15 dibasic acid and C16 dibasic acid. More preferably, the long-chain dibasic acid is at least one or more of C10 to C16 dibasic acids, or at least one or more of n-C10 to C16 dibasic acids, e.g. at least one selected from the group consisting of sebacic acid, undecanedioic acid, dodecanedioic acid, tridecanedioic acid, tetradecanedioic acid, pentadecanedioic acid and hexadecanedioic acid.

Preferably, the length of the long-chain dibasic acid impurity of shorter carbon-chain is less than that of the long-chain dibasic acid. Preferably, the content of the long-chain dibasic acid impurity of shorter carbon-chain, compared to that produced in a fermentation process by using a conventional microorganism, is decreased by at least 5%, preferably at least 10%, preferably at least 20%, more preferably at least 40%, more preferably at least 50% or more.

In some embodiments, the method of modifying a long-chain dibasic acid producing microorganism strain comprises steps of:

1) preparing a target gene fragment having a mutation by error-prone PCR;
2) preparing fragments upstream and downstream of the target gene necessary for homologous recombination as templates for homologous recombination with a resistance marker gene, preferably the resistance marker gene is hygromycin B;

3) preparing a complete recombination fragment by PCR overlap extension;

4) introducing the recombination fragment into a strain by homologous recombination;

5) screening positive strains by means of the resistance marker;

6) screening strains wherein the content of the long-chain dibasic acid impurity of shorter carbon-chain is decreased; and 7) optionally, removing the resistance maker in the screened strains by further homologous recombination.

The present invention also relates to an isolated mutated promoter, which, relative to the sequence set forth in SEQ ID NO: 25, have a mutation of bases AAAAAAAAAA at positions 266-275 to bases AAAAAAAAA, e.g. having a mutation 275delA, and preferably comprises or consists of SEQ ID NO: 26, or has at least 70%, e.g. at least about 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95% or 99.96% sequence identity thereto.

The present invention also relates to a microorganism containing the mutated promoter, wherein the promoter directs the expression of POX gene (Genbank Accession Number M12161, and the amino acid coding sequence is e.g. set forth at positions 457-2445 in SEQ ID NO: 24). Preferably, the microorganism is selected from the group consisting of *Corynebacterium, Geotrichum candidum, Candida, Pichia, Rhodotroula, Saccharomyces* and *Yarrowia*, more preferably the microorganism is yeast, and more preferably the microorganism is *Candida tropicalis* or *Candida sake*. In some embodiments, the microorganism is CCTCC M2011192 or CCTCC M203052.

The present invention also relates to a method for producing a long-chain dibasic acid by using the microorganism containing the mutated promoter, comprising culturing the microorganism, and optionally isolating and/or purifying the long-chain dibasic acid from the culture product.

In some embodiments, the long-chain dibasic acid is selected from C9 to C22 long-chain dibasic acids, preferably selected from C9 to C18 long-chain dibasic acids, more preferably comprises one or more selected from the group consisting of C10 dibasic acid, C11 dibasic acid, C12 dibasic acid, C13 dibasic acid, C14 dibasic acid, C15 dibasic acid and C16 dibasic acid. More preferably, the long-chain dibasic acid is at least one or more of C10 to C16 dibasic acids, or at least one or more of n-C10 to C16 dibasic acids, e.g. at least one selected from the group consisting of sebacic acid, undecanedioic acid, dodecanedioic acid, tridecanedioic acid, tetradecanedioic acid, pentadecanedioic acid and hexadecanedioic acid.

In the present invention, the existing *Candida tropicalis* strain CATN145 (Deposit No. CCTCC M2011192) is used as the starting strain, and error-prone PCR method is used to mutate the promoter of the key gene, POX gene, in the β-oxidation, and the gene is subjected to directed evolution by a homologous recombination method, so as to screen for a long-chain dibasic acid producing strain with significantly decreased content of long-chain dibasic acid impurity of shorter carbon-chain. By screening, the present invention obtains a strain in which the content of acid impurity of shorter carbon-chain is significantly decreased, and it is named as mutant strain 526. By sequencing analysis, it is found that, compared to parental strain CCTCC M2011192, taking the first base upstream of the start codon ATG as −1, the POX gene of the mutant strain 526 has a mutation −182_−191AAAAAAAAAA>AAAAAAAAA, e.g. a base mutation −182delA, in its promoter region.

According to the present invention, the sequence of the POX gene of *Candida tropicalis* is set forth in SEQ ID NO: 16, 26, 27 or 29.

After further removing the resistance marker from the mutant strain, compared to the original strain, the mass ratio of acid impurity of shorter carbon-chain in the fermentation broth after fermentation is significantly decreased, and the content of acid impurity of shorter carbon-chain in the final long-chain dibasic acid product obtained after extraction and purification of the fermentation broth is decreased to less than 200 ppm. The acid impurity of shorter carbon-chain is a long-chain dibasic acid impurity of shorter carbon-chain whose number of carbon atoms is less than that of the fermentation product long-chain dibasic acid.

For example, when the fermentation product is C12 long chain dibasic acid such as dodecanedioic acid, the acid impurity of shorter carbon-chain is predominantly C10 dibasic acid, such as sebacic acid.

According to the present invention, a strain with a base mutation in the promoter region of the POX gene is screened by directed evolution of the gene, and when the strain is used to produce a long-chain dibasic acid by fermentation, the content of a long-chain dibasic acid impurity of shorter carbon-chain is significantly decreased. A long-chain dibasic acid product with high purity and low content of long-chain dibasic acid impurity of shorter carbon-chain can better meet quality requirements of high-grade polyamide, polyesters and other products, and the performances of prepared polymer products are more excellent. More importantly, this greatly reduces the difficulty of subsequent extraction and purification processes of dibasic acids, simplifies the process, and saves energy consumption.

BRIEF DESCRIPTION OF THE DRAWINGS

FIG. 2 is the alignment of the nucleotide sequences of the POX genes of the mutant strain 526 of the invention (SEQ ID NO: 16) and the original strain 192 (nucleotides 1-545 of SEQ ID NO: 28), and the mutation sites are boxed with a black box, wherein 192 refers to CCTCC M2011192.

DETAILED DESCRIPTION OF THE INVENTION

Definitions

Figure 1:
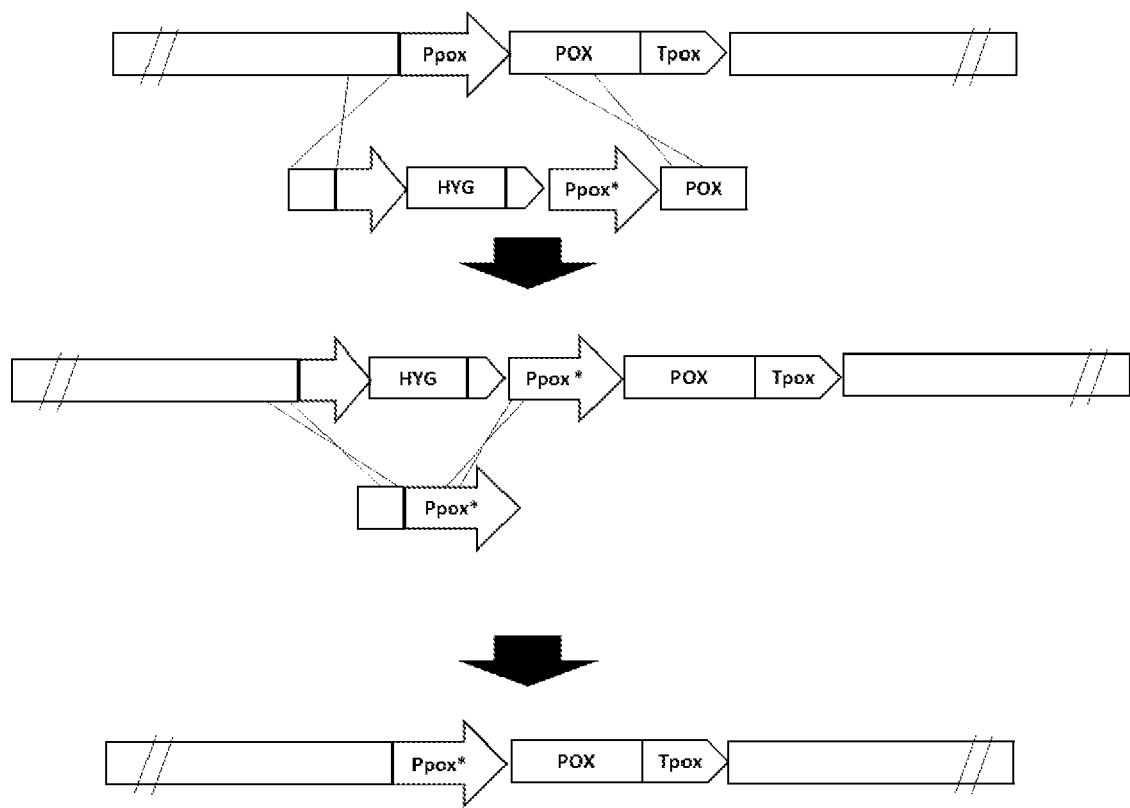
FIG. 1 is a scheme of the integration of the POX gene with mutations and the removal of the hygromycin resistance marker by homologous recombination. "*" indicates the mutations that may be present in any region of POX (including the promoter, coding region, and terminator).

Unless defined otherwise, technical and scientific terms used herein have the same meanings as commonly understood by skilled persons in the art. See e.g. Singleton et al., DICTIONARY OF MICROBIOLOGY AND MOLECULAR BIOLOGY 2$^{nd}$ ed., J. Wiley & Sons (New York, N.Y. 1994); Sambrook et al., MOLECULAR CLONING, A LABORATORY MANUAL, Cold Springs Harbor Press (Cold Springs Harbor, 1989).

Long chain alkane: the fermentation substrate of the invention comprises a long chain alkane, belonging to a saturated hydrocarbon, which is a saturated hydrocarbon among hydrocarbons; its whole structure is mostly composed only of carbon, hydrogen, carbon-carbon single bond, and carbon-hydrogen single bond. It includes an alkane of the formula $CH_3(CH_2)_nCH_3$, where $n \geq 7$. Preferred are n-C9-C22 alkanes, more preferred are n-C9-C18 alkanes, and most preferred are n-C10, n-C11, n-C12, n-C13, n-C14, n-C15 or n-C16 alkanes.

Long-chain dibasic acid (LCDA; also known as long chain dicarboxylic acid or long chain diacid, hereinafter abbreviated as dibasic acid sometimes) includes a diacid of the formula $HOOC(CH_2)_nCOOH$, where $n \geq 7$. Preferably, the long-chain dibasic acid is selected from C9-C22 long-chain dibasic acids, preferably C9-C18 long-chain dibasic acids; more preferably comprises one or more of C10 dibasic, C11 dibasic acid, C12 dibasic acid, C13 dibasic acid, C14 dibasic acid, C15 dibasic acid and C16 dibasic acid. Preferably, the long-chain dibasic acid is at least one or more of C10 to C16 dibasic acids, and preferably at least one or more of n-C10 to C16 dibasic acids, e.g. at least one selected from the group consisting of sebacic acid, undecanedioic acid, dodecanedioic acid, tridecanedioic acid, tetradecanedioic acid, pentadecanedioic acid and hexadecanedioic acid.

Long-chain dibasic acid producing microorganism: the strain that has been reported to produce and accumulate a dibasic acid includes bacterium, yeast, and mold, such as *Corynebacterium, Geotrichum candidum, Candida, Pichia, Rhodotroula, Saccharomyces, Yarrowia*, and the like. Among them, many species of *Candida* are good strains for the production of a dibasic acid by fermentation. The strain for fermentation preferably includes: *Candida tropicalis* or *Candida sake*.

A fermentation substrate xC/Cx long-chain alkane (x is the number of carbon atoms, C is carbon, and x=9 to 22) during a process of producing a long-chain dibasic acid by fermentation, is oxidized into xC/Cx long-chain dibasic acid by the strain (x is the number of carbon atoms, C is carbon, and x=9-22). However, due to β-oxidation, some strains may degrade the produced xC/Cx long-chain dibasic acid into yC/Cy long-chain dibasic acid impurity of shorter carbon-chain whose number of carbon atoms is less than that of the original long-chain alkane (y is the number of carbon atoms, C is carbon, and y<x). These long-chain dibasic acid impurities of shorter carbon-chain are very similar to those of desired xC/Cx long-chain dibasic acid to be obtained in characteristics, and are difficult to be effectively separated by conventional means. These long-chain dibasic acid impurities of shorter carbon-chain may enter into the final dibasic acid product along with subsequent treatment processes, thereby greatly influencing purity and quality of the dibasic acid product. Preferably, when the chemical formula of the long-chain dibasic acid is $HOOC(CH_2)_nCOOH$, where $n \geq 7$, the chemical formula of the long-chain dibasic acid impurities of shorter carbon-chain is $HOOC(CH_2)_mCOOH$, where m<n, and both m and n are integers.

In some embodiments, C10 dibasic acid (e.g. sebacic acid) is the main long-chain dibasic acid impurity of shorter carbon-chain during the process of producing C12 dibasic acid (e.g. dodecanedioic acid) by fermentation, which accounts for more than 30%, more than 40%, more than 50%, more than 60%, more than 65%, more than 70%, more than 75%, more than 80%, more than 85%, more than 90%, more than 95%, more than 96%, more than 97% or more of the total long-chain dibasic acid impurities of shorter carbon-chain.

When a long-chain dibasic acid is produced by fermentation in the present invention, the fermentation broth after fermentation contains a long-chain dibasic acid impurity of shorter carbon-chain, the content of which is significantly decreased compared with that of long-chain dibasic acid impurity of shorter carbon-chain produced by a conventional microbiological fermentation method, such as a fermentation method using a non-mutant microorganism according to the present invention, such as decreased by at least 5%, 6%, 7%, 8%, 9%, 10%, 12%, 14%, 16%, 18%, 20%, 25%, 30%, 35%, 40%, 50%, 60%, 70%, 80%, 90%, 95% or more, preferably by at least 10%, more preferably by at least 20%, more preferably by at least 40%, more preferably by at least 50%, more preferably by at least 70% or more. The decrease specifically refers to a reduction of a certain specific long-chain dibasic acid impurity of shorter carbon-chain which is shorter than the target long-chain dibasic acid. For example, when C12 dibasic acid such as dodecanedioic acid is produced by fermentation in the present invention, the content of sebacic acid is significantly decreased, such as by at least 5%, 6%, 7%, 8%, 9%, 10%, 12%, 14%, 16%, 18%, 20%, 25%, 30%, 35%, 40%, 50%, 60%, 70%, 80%, 90%, 95% or more.

As used herein, that the content of the impurity is substantially or significantly decreased refers to that the content of the impurity, compared to the reference, is decreased by at least 5%, 6%, 7%, 8%, 9%, 10%, 12%, 14%, 16%, 18%, 20%, 25%, 30%, 35%, 40%, 50%, 60%, 70%, 80%, 90%, 95% or more, preferably by at least 10%, more preferably by at least 20%, more preferably by at least 40%, more preferably by at least 50%, more preferably by at least 70% or more.

The term "isolated", when applied to a nucleic acid, means that the nucleic acid is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography.

As used herein, the expression "relative to the GenBank Accession Number M12161" or "relative to SEQ ID NO: 25" refers to a mutation at a corresponding position when aligned with the sequence of GenBank Accession Number M12161 or SEQ ID NO: 25). The corresponding position refers to the numbering of the residue of a reference sequence (SEQ ID NO: 25) when a given polynucleotide sequence (e.g. a mutated POX gene or promoter sequence) is compared to the reference sequence. A base in a nucleic acid "corresponds" to a given base when it occupies the same essential structural position within the nucleic acid as the given base. In general, to identify corresponding positions, the sequences of nucleic acids are aligned so that the highest order match is obtained (see, e.g. Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carillo et al. (1988) SIAM J Applied Math 48: 1073). Alignment of nucleotide sequences also can take into account conservative differences and/or frequent substitutions in nucleotides. Conservative differences are those that preserve the physico-chemical properties of the residues involved. Alignments can be global (alignment of the compared sequences over the entire length of the sequences and including all residues) or local (alignment of a portion of the sequences that includes only the most similar region(s)).

As used herein, the base mutation "XXX delA" means that the base A at position XXX is deleted.

As used herein, the base mutation "-182_-191AAAAAAAAAA>AAAAAAAAA" or "266_275 AAAAAAAAAA>AAAAAAAAA" means that the ten "A"s at positions -182 to -192 or 266 to 275 are mutated to 9 "A"s due to deletion of one A. The deleted base A can be an A at any position of these positions.

Herein, where a base is mentioned, G refers to guanine, T refers to thymine, A refers to adenine, C refers to cytosine, and U refers to uracil.

As used herein, the "non-mutated POX gene" refers to a POX gene that does not comprises the mutation -182delA (275delA with reference to SEQ ID NO: 25) or -182_-191AAAAAAAAAA>AAAAAAAAA (266_275 AAAAAAAAAA>AAAAAAAAA with reference to SEQ ID NO: 25) according to the invention, e.g. a naturally occurring wild type allele, such as the POX gene with the Accession Number M12161 in the GenBank. An example of non-mutated POX gene is set forth in SEQ ID NO: 24. The non-mutated POX gene may contain other mutations, such as a silent mutation in the coding region which does not result in the alteration of the encoded amino acid.

As used herein, "non-mutant microorganism" refers to a microorganism which does not contain the mutated POX gene or homologous gene thereof according to the invention, e.g. contain only the POX gene with the Accession Number M12161 in the GenBank. In an embodiment, the non-mutant microorganism contains a non-mutated POX gene according to the invention.

In some embodiments, a long-chain dibasic acid is produced by a microbiological fermentation method, and the fermentation broth contains a long-chain dibasic acid impurity of shorter carbon-chain, the content of which is decreased to less than 1.5%, such as less than 1.4%, 1.3%, 1.2%, 1.1%, 1.0%, 0.9%, 0.8%, 0.7%, 0.6%, 0.5%, 0.4%, 0.3% or less, preferably less than 1.0%, more preferably less than 0.6%, more preferably less than 0.4%, wherein the percentage is the mass percentage of the long-chain dibasic acid impurity of shorter carbon-chain to the long-chain dibasic acid in the fermentation broth.

The long-chain dibasic acid produced by the microbiological fermentation method according to the present invention contains a long-chain dibasic acid impurity of shorter carbon-chain, wherein the content of the long-chain dibasic acid impurity of shorter carbon-chain is less than 500 ppm, preferably less than 400 ppm, preferably less than 300 ppm, preferably less than 250 ppm, more preferably less than 200 ppm, more preferably less than 150 ppm, and even more preferably less than 100 ppm.

In one embodiment of the present invention, when C12 long-chain dibasic acid e.g. dodecanedioic acid is produced by a microbiological fermentation method, the long-chain dibasic acid impurity of shorter carbon-chain is predominantly C10 long-chain dibasic acid, wherein the content of C10 long-chain dibasic acid impurity is less than 350 ppm, preferably less than 300 ppm, 290 ppm, 280 ppm, 270 ppm, 260 ppm, 250 ppm, 240 ppm, 230 ppm, 220 ppm or 210 ppm, more preferably less than 200 ppm, 180 ppm, 160 ppm, 150 ppm or less.

The unit "ppm" of the impurity content in the present invention is the mass ratio of the impurity to the long-chain dibasic acid, and 100 ppm=$100*10^{-6}$=0.01%.

The method for assaying dibasic acid and the impurity content may employ the techniques well known to those skilled in the art, such as an internal standard method or a normalization method of gas chromatography detection.

POX gene encodes acetyl coenzyme A oxidase. There are three POX genes in the preferable fermentation strain *candida tropicalis*, i.e. POX2, POX4 and POX5. Proteins coded by these three genes are considered to participate in the β-oxidation pathway in an octamer form, and are responsible for degradation of fatty acids and derivatives thereof.

Homologous genes refer to two or more gene sequences with at least 80% similarity, including orthologous genes, paralogous genes and/or xenologous genes. The homologous gene of the POX gene in the invention refers to either the orthologous gene of the POX gene, or paralogous gene or xenologous gene of the POX gene.

Sequence identity refers to the percentage of the residues of a polynucleotide sequence variant that are identical to a non-variant sequence after sequence alignment and introduction of a gap. In a particular embodiment, the polynucleotide variant has at least about 70%, at least about 75%, at least about 80%, at least about 90%, at least about 95%, at least about 96%, at least about 97%, at least about 98%, at least about 99%, at least about 99.1%, at least about 99.2%, at least about 99.3%, 99.4%, at least about 99.5%, at least about 99.6%, 99.7%, at least about 99.8%, at least about 99.9%, at least about 99.91%, at least about 99.92%, at least about 99.93%, at least about 99.94%, at least about 99.95%, or at least about 99.96% polynucleotide homology described herein.

As used herein, the terms "homology" and "identity" are used interchangeably herein and refer to the extent of non-variance of nucleotide sequences, which can be detected through the number of identical nucleotide bases by aligning a polynucleotide with a reference polynucleotide. The sequence identity can be determined by standard alignment algorithm programs used with default gap penalties established by each supplier. Homologous nucleic acid molecules refer to a pre-determined number of identical or homologous nucleotides. Homology includes substitutions that do not change the encoded amino acid ("silent substitution") as well as identical residues. Substantially homologous nucleic acid molecules hybridize typically at moderate stringency or high stringency all along the length of the nucleic acid or along at least about 70%, 80% or 90% of the full-length nucleic acid molecule of interest. Nucleic acid molecules that contain degenerate codons in place of codons in the hybridizing nucleic acid molecule are also contemplated in the invention. Whether any two nucleic acid molecules have nucleotide sequences that are at least 80%, 85%, 90%, 95%, 96%, 97%, 98% or 99% "identical" can be determined using a known computer algorithm such as the BLASTN, FASTA, DNAStar and Gap (University of Wisconsin Genetics Computer Group (UWG), Madison Wis., USA). Percent homology or identity of nucleic acid molecules can be determined, e.g. by comparing sequence information using a GAP computer program (e.g., Needleman et al. J. Mol. Biol. 48: 443 (1970), as revised by Smith and Waterman (Adv. Appl. Math. 2: 482 (1981)). Briefly, a GAP program defines similarity as the number of aligned symbols (i.e., nucleotides) which are similar, divided by the total number of symbols in the shorter of the two sequences.

Directed evolution refers to a process of simulating a natural selection by technological means. Through an artificially created mutation and specific screening pressure, a protein or nucleic acid is mutated in a specific direction, thereby realizing an evolutionary process in nature that requires thousands of years to complete in a short period of time at the molecular level. The methods for performing directed evolution are known in the art, e.g. error-prone PCR (e.g. Technique, 1, 11-15, 1989; Genome Research, 2, 28-33, 1992).

In some embodiments, in the error-prone PCR of the invention, the concentration of $Mg^{2+}$ is in a range of 1 to 10 mM, preferably 2 to 8 mM, more preferably 5 to 6 mM, and/or the concentration of dNTP is from 0.1 to 5 mM, preferably from 0.2 to 3 mM, more preferably 0.5 to 2 mM, and more preferably from 0.8 to 1.5 mM, for example 1 mM, and/or addition of freshly prepared $MnCl_2$ to a final concentration of 0.1 to 5 mM, preferably 0.2 to 2 mM, more preferably 0.3 to 1 mM, and more preferably 0.4 to 0.7 mM, such as 0.5 mM. In some embodiments, the rate of mutation is increased by decreasing the amount of template and appropriately increasing PCR cycles to 40 or more, e.g. 41, 42, 43, 44, 45, 46, 47, 48, 49, 50, 55, 60 or more PCR cycles.

PCR overlap extension, also known as SOE (gene splicing by overlap extension) PCR, refers to a method of splicing different DNA fragments together through PCR amplification by designing primers having complementary ends.

Homologous recombination refers to a recombination between DNA molecules depending on sequence similarity, and is most commonly found within cells for repairing mutations generated during mitosis. Homologous recombination technology has been widely used in genome editing, including gene knockout, gene repair, and introduction of a new gene to a specific site, etc. A class of microorganisms represented by *Saccharomyces cerevisiae* has a high probability of homologous recombination in cells, which does not depend on sequence specificity, and has obvious advantages in genome editing. While site-specific recombination, depending on the involvement of specific site and site-specific recombinase, occurs only between specific sites, such as Cre/loxP, FLP/FRT, and the like. The homologous recombination technique used in this patent does not belong to site-specific recombination, and the recombination depends on the intracellular DNA repair system.

Resistance marker refers to one of selectable markers that often have the ability to confer a transformant survival in the presence of an antibiotic. The resistance marker gene includes NPT, HYG, BLA, CAT, etc., which can be resistant to kanamycin, hygromycin, ampicillin/carbenicillin, and chloramphenicol, etc., respectively. Preferably, the resistance marker gene is hygromycin B. The resistance maker gene is hygromycin B resistance gene HYG.

During fermentation, the fermentation medium comprises: a carbon source, a nitrogen source, an inorganic salt, and a nutritional factor.

In some embodiments, the carbon source includes one or more selected from the group consisting of glucose, sucrose, and maltose; and/or the carbon source is added in an amount of 1% to 10% (w/v), such as 1.5%, 2.0%, 2.5%, 3.0%, 3.5%, 4.0%, 4.5%, 5.0%, 6.0%, 7.0%, 8.0%, or 9.0%.

In some embodiments, the nitrogen source includes one or more selected from the group consisting of peptone, yeast extract, corn syrup, ammonium sulfate, urea, and potassium nitrate; and/or the nitrogen source is added in a total amount of 0.1% to 3% (w/v), such as 0.2%, 0.4%, 0.5%, 0.6%, 0.8%, 1.0%, 1.2%, 1.5%, 1.8%, 2.0%, or 2.5%.

In some embodiments, the inorganic salt includes one or more selected from the group consisting of monopotassium phosphate, potassium chloride, magnesium sulfate, calcium chloride, ferric chloride, and copper sulfate; and/or the inorganic salt is added in a total amount of 0.1% to 1.5% (w/v), such as 0.2%, 0.3%, 0.4%, 0.5%, 0.6%, 0.7%, 0.8%, 0.9%, 1.0%, 1.1%, 1.2%, 1.3%, or 1.4%.

In some embodiments, the nutritional factor includes one or more selected from the group consisting of vitamin B1, vitamin B2, vitamin C, and biotin; and/or the nutritional factor is added in a total amount of 0 to 1% (w/v), such as 0.2%, 0.3%, 0.4%, 0.5%, 0.6%, 0.7%, 0.8%, or 0.9%. According to common knowledge in the field of fermentation, the percentage in the present invention is mass-to-volume ratio, i.e., w/v; % means g/100 mL.

Those skilled in the art can easily determine the amount of the above substances to be added.

In one embodiment of the present invention, the inoculation amount of the fermentation strain is 10% to 30%, such as 11%, 12%, 13%, 14%, 15%, 16%, 17%, 18%, 19%, 20%, 22%, 24%, 25%, 27%, or 29%. When the strain is cultured until the optical density ($OD_{620}$) of bacterial cells is more than 0.5 (dilution by 30 folds), a substrate is added for conversion by fermentation.

Extraction and purification of long-chain dibasic acid: the fermentation broth obtained by fermentation is subject to extraction and purification treatment to obtain a final long-chain dibasic acid product. The steps of extraction and purification include: sterilization and acidification of the fermentation broth, as well as acidification, solid-liquid separation, and/or solvent crystallization of the obtained clear liquid.

The extraction and purification according to the present invention may be repeated more than once, and multiple rounds of the extraction and purification steps contribute to further reduce the impurity content in a dibasic acid product. For example, C12 long-chain dibasic acid product obtained by the present invention was further treated by referring to the refining process in Example 1 of the Chinese patent CN 101985416 A, resulted in C10 long-chain dibasic acid with a content of 520 ppm, and by further extraction and purification or refinement, the content of C10 long-chain dibasic acid was effectively decreased to less than 200 ppm, such as less than 180 ppm, less than 160 ppm, 140 ppm, 120 ppm or less.

The fermentation broth includes a fermentation broth containing a salt of a long-chain dibasic acid produced during a process for producing the long-chain dibasic acid by biological fermentation, and the fermentation broth containing a salt of a long-chain dibasic acid may contain sodium salt of a long-chain dibasic, potassium salt of a long-chain dibasic acid or ammonium salt of a long-chain dibasic acid, etc.

The sterilization is preferably membrane filtration: impurity such as residual bacteria and large proteins, etc. is effectively separated from the fermentation broth containing a salt of a long-chain dibasic acid by a filter membrane. Further, a ceramic membrane filtration process is preferred. When a ceramic membrane is used for membrane filtration, preferably, the pre-membrane pressure is 0.2 to 0.4 MPa; and preferably, the pore diameter of the filter membrane is 0.05 to 0.2 µm.

The acidification refers to an acidification treatment of a membrane clear liquid containing a salt of a long-chain dibasic acid obtained after membrane filtration, and the salt of the long chain dibasic acid is converted to a precipitate of the long chain dibasic acid by adding an acid. The acidification is preferably carried out using an inorganic acid such as sulfuric acid, hydrochloric acid, nitric acid, or an acid mixture thereof. The amount of the inorganic acid added during the acidification treatment needs to sufficiently precipitate the long-chain dibasic acid in the solution, and is mainly based on the end point pH of the solution. Preferably, the end point pH of acidification is less than 5, and more preferably the end point pH is less than 4.0. When an inorganic acid is added for acidification, a precipitate of a long-chain dibasic acid and a corresponding inorganic salt solution can be obtained.

The solid-liquid separation refers to separation of the obtained long-chain dibasic acid precipitate from the acidification mother liquor, which includes separation by filtration or/and centrifugation, and a commonly used solid-liquid separation apparatus can be used.

Preferably, the step of extraction and purification further includes decoloration of the fermentation broth containing a salt of a long-chain dibasic acid, comprising adding activated carbon to the fermentation broth or the membrane clear liquid containing a salt of a long-chain dibasic acid for decoloration treatment, and then removing the activated carbon by filtration after the decoloration treatment. The decoloration step can further remove impurities from the long-chain dibasic acid solution. Preferably, the activated carbon is added in an amount of 0.1 to 5 wt % and preferably 1 to 3 wt % (relative to the amount of the long-chain dibasic acid contained in the solution).

The solvent crystallization refers to dissolving the long-chain dibasic acid precipitate in an organic solvent, and crystallizing the long-chain dibasic acid by cooling\evaporation\solvating-out, and then separating the crystals to obtain a more purified long-chain dibasic acid. The organic solvent includes one or more of alcohol, acid, ketone, and ester; wherein, the alcohol includes one or more of methanol, ethanol, isopropanol, n-propanol, and n-butanol; the acid includes acetic acid; the ketone includes acetone; and the ester includes ethyl acetate and/or butyl acetate.

In another preferred embodiment, the precipitate of a long-chain dibasic acid is dissolved in an organic solvent and then decolorized, and then is separated to obtain a clear liquid and a more purified long-chain dibasic acid. When activated carbon is used for decoloration, the decoloration temperature is 85 to 100° C., and the decoloration time is 15 to 165 min. In another preferred embodiment, after being separated, the clear liquid is subjected to cooling crystallization. The cooling crystallization may include the following steps: firstly, cooling to 65 to 80° C., incubating for 1 to 2 hours, then cooling to 25 to 35° C., and crystallizing. In another preferred embodiment, after crystallization, the resulting crystals are separated, thereby obtaining long-chain dibasic acid. The method for separating the crystals can be centrifugal separation.

In some embodiments, the present invention relates to production of nylon filaments, engineering plastics, synthetic perfumes, cold-resistant plasticizers, high-grade lubricating oils and polyamide hot melt adhesives by using the dibasic acid product obtained above.

As used herein, "optional" or "optionally" means that the subsequently described event or circumstance does or does not occur, and that the description comprises instances where the event or circumstance occurs or does not occur. For example, "optionally a step" means that the step is present or not present.

As used herein, the term "about" means a range of values including the specified value, which a person of ordinary skill in the art would consider reasonably similar to the specified value. In some embodiments, the term "about" means within a standard deviation using measurements generally acceptable in the art. In some embodiments, "about" means a range extending to +/−10% of the specified value.

The present invention will be further illustrated by following non-limiting examples. It is well known to those skilled in the art that modifications may be made to the invention without departing from the spirit of the present invention, and such modifications are also within the scope of the present invention.

The following experimental methods are conventional methods unless otherwise specified, and the experimental materials used can be easily obtained from commercial companies unless otherwise specified.

Example 1 Medium, Culture and Fermentation Method, and Detection Method of Dibasic Acid 1. The formulation of YPD medium: 2% of peptone, 2% of glucose and 1% of yeast extract (OXOID, LP0021). For solid medium, 1.5% to 2% of agar powder was further needed to add.

In culturing, single colonies were taken into a 2 mL centrifuge tube containing 1 ml of YPD liquid medium, and cultured on a shaker at 30° C., 250 RPM for 1 day.

2. The formulation of seed medium: sucrose 10 to 20 g/L (specifically used 10 g/L), yeast extract 3 to 8 g/L (specifically used 3 g/L), corn syrup for industrial fermentation (referred to as corn syrup, with a total nitrogen content of 2.5 wt %) 2 to 4 g/L (specifically used 2 g/L), $KH_2PO_4$ 4 to 12 g/L (specifically used 4 g/L), urea 0.5 to 4 g/L (specifically used 0.5 g/L) (sterilized separately at 115° C. for 20 min), and a fermentation substrate of n-dodecane, 20 mL/L.

In culturing, a cultured bacterial solution obtained in step 1 was placed in a 500 mL shake flask containing 30 mL of the seed medium with an inoculation amount of 3-5%, and cultured on a shaker at 250 rpm, 30° C. until the $OD_{620}$ reached 0.8 (dilution by 30 folds).

3. Fermentation medium (w/v): sucrose 10 to 40 g/L (specifically used 10 g/L), corn syrup (with a total nitrogen content of 2.5 wt %) 1 to 5 g/L (specifically used 1 g/L), yeast extract 4 to 12 g/L (specifically used 4 g/L), NaCl 0 to 3 g/L (specifically not used), $KNO_3$ 4 to 12 g/L (specifically used 4 g/L), $KH_2PO_4$ 4 to 12 g/L (specifically used 4 g/L), urea 0.5 to 3 g/L (specifically used 0.5 g/L) (sterilized separately at 115° C. for 20 min), a fermentation substrate of n-dodecane, 300 to 400 mL/L (specifically used 300 mL/L), and acrylic acid 4 g/L, wherein the pH was adjusted to 7.5-7.6 with 1N HCl or 1N NaOH.

In fermentation, a seed solution obtained in step 2 was inoculated into a 500 mL shake flask containing 15 mL of the fermentation medium with an inoculation amount of 10-30%, and cultured on a shaker at 30° C., 250 rpm for 90 to 144 h. During culturing, the pH was adjusted to a set range by adding acid/base at intervals.

4. Steps for determining the yield of dibasic acid and the content of long-chain dibasic acid impurity of shorter carbon-chain by gas chromatography (GC)

(1) Detection of the content of the product and impurity in the fermentation broth: the fermentation broth was subjected to conventional gas chromatography pretreatment and detected by gas chromatography (internal standard method). The chromatography conditions were as follows:

Chromatography column: Supelco SPB-50 30 m*0.53 mm*0.5 μm (cat. No.: 54983).

Gas chromatograph (Shimadzu, GC-2014).

Method: the initial temperature was 100° C., and the temperature was raised to 230° C. at a rate of 15° C./min, and kept for 2 min. The carrier gas was hydrogen, the inlet temperature was 280° C., the FID temperature was 280° C., and the injection volume was 4 μL.

The yield of the dibasic acid was calculated from the ratio of the peak area of the dibasic acid product to the peak area of the internal standard with known concentration, and the content of the impurity was calculated from the peak area of the dibasic acid product and the peak area of the impurity.

(2) Detection of the purity and impurity content in the solid product: the solid product was subjected to conventional gas chromatography pretreatment and detected by gas chromatography (normalization method).

Chromatography conditions: chromatographic column: Supelco SPB-50 30 m*0.53 mm*0.5 μm (cat. No.: 54983).

Gas chromatograph (Shimadzu, GC-2014).

Method: the initial temperature was 100° C., and the temperature was raised to 230° C. at a rate of 15° C./min, and held for 2 min. The carrier gas was hydrogen, the inlet temperature was 280° C., the FID temperature was 280° C., and the injection volume was 4 μL.

The purity of the product and the content of the impurity were calculated from the peak area of the dibasic acid product and the peak area of the impurity.

Embodiment 2 Preparation of Recombination Template with POX Promoter Mutation

1. Cloning of POX4 Promoter
(1) Extraction of Total RNA and Transcriptome Sequencing Single colonies of *Candida tropicalis* CCTCC M2011192 was inoculated in a 2 mL Eppendorf tube with 1 mL of the YPD medium of Example 1, and cultured at 30° C. on a shaker at 250 rpm for one day. The above bacterial solution was inoculated in a 500 mL flask with 30 mL of the seed medium of Example 1, in which the inoculation amount is 3%, and cultured at 30° C. at 250 rpm until $OD_{620}$ reached 0.8. The seed solution was inoculated in a 500 mL flask with 15 mL of the fermentation medium of Example 1, in which the inoculation amount is 20%. The bacteria were cultured at 30° C. at 250 rpm for 36 hours, and collected by centrifuge at 3000 g for 5 min. The substrate for fermentation in the fermentation medium was n-dodecane at 400 mL/L. During the culturing, pH was adjusted to 7.5-7.6 by 1N HCl or 1N NaOH intermittently.

RNA extraction was carried out by using TRNzol universal Reagent kit (Tiangen), and disrupting cells by grounding the cells with liquid nitrogen. The Miseq platform (Illumina) was employed to perform the transcriptome sequencing by means of two-ends sequencing method. 20M Reads with a length of 2×251 bp were obtained. The obtained Reads were removed of linker and filtered of low-quality bases and Reads, and assembled to Unigene by using the Trinity software (trinityrnaseq.sf.net), and the note of function was made by using Non-Redundant protein database of the NCBI.

(2) Bioinformatics Analysis

Local blast (Blast+2.7.1) was used to construct library on the obtained Unigene, and using a known acetyl coenzyme A oxidase I gene (M12161) from *Candida tropicalis* as query, one candidate POX gene was obtained by tblastn search, whose sequence was set forth in SEQ ID NO: 28.

2. Preparation of POX Promoter Mutation Template

The genomic DNA of *Candida tropicalis* CCTCC M2011192 was extracted by using Ezup Yeast Genomic DNA Extraction Kit (Sangon, Cat No. 518257). The method with liquid nitrogen grinding was used in favor of increasing the cell wall disruption efficiency. Genomic DNA obtained by this method was used as template for error-prone PCR. The obtained mutation-free product was called POX and was confirmed by sequencing to be identical to the sequence set forth by GenBank Accession Number: M12161.

3. Error-Prone PCR

The concentration of $Mg^{2+}$ was adjusted (2-8 mM, increasing by 0.5 mM) and the promoter of POX gene was amplified by error-prone PCR using Taq DNA polymerase (Takara, Cat No. R001B). The primers were as follows:

Ppox-F:
(SEQ ID NO. 1)
5'-GTGATTTGGCACTTGACAG-3'

Ppox-R:
(SEQ ID NO. 2)
5'-TTTTGAAGTTCGGTAGGCAT-3'

PCR reaction conditions were:
Step 1: 98° C. for 30 s,
Step 2: 98° C. for 10 s, 52° C. for 30 s, 72° C. for 1 m, 35 cycles,
Step 3: 72° C. for 5 m.

The PCR product was subjected to 1% agarose gel electrophoresis and recovered and purified by using the Axygen Gel Recovery Kit (Axygen, AP-GX-250G).

Example 3 Preparation of Homologous Recombination Template

All DNA fragments in this example were obtained by amplification using Takara's PrimeSTAR® HS high-fidelity DNA polymerase (Takara, R040A). After electrophoresis on 1% agarose gel, the purified DNA fragment was recovered using the Axygen Gel Recovery Kit (Axygen, AP-GX-250G).

1 Amplification of the upstream and downstream homologous recombination fragments. The template was the genomic DNA of *Candida tropicalis* (supra). The primer sequences were as follows:

POX_Upstream-F:
(SEQ ID NO. 3)
5'-ACAACAACGAAGAAGACTCA-3'

POX_Upstream-R:
(SEQ ID NO. 4)
5'-CCCATTTCTTCCTCCAATCA-3'

POX_Downstream-F:
(SEQ ID NO. 5)
5'-ATGCCTACCGAACTTCAAAA-3'

POX_Downstream-R:
(SEQ ID NO. 6)
5'-TCTTTGTTGGTCTTTGGTCA-3'.

The PCR reaction conditions were as follows:
Step 1: 98° C. for 30 s
Step 2: 98° C. for 10 s, 55° C. for 30 s, 72° C. for 25 s, 30 cycles
Step 3: 72° C. for 5 m.

The obtained products were designated as POX_Upstream and POX_Downstream, respectively, and verified by sequencing, the sequences thereof were set forth in SEQ ID NOs. 17 and 18.

2 Amplification of the resistance screening marker (HYG, hygromycin resistance gene). The amplification template was the vector pCIB2 (SEQ ID NO.19) owned by our company. The primer sequences were as follows:

POX_HYG-F:
(SEQ ID NO. 7)
5'-TGATTGGAGGAAGAAATGGGGCATGCGAACCCGAAAATGG-3'

POX_HYG-R:
(SEQ ID NO. 8)
5'-CTGTCAAGTGCCAAATCACGCTAGCAGCTGGATTTCACT-3'.

The PCR reaction conditions were as follows:
Step 1: 98° C. for 30 s,
Step 2: 98° C. for 10 s, 55° C. for 10 s, 72° C. for 1 m 50 s, 5 cycles,
Step 3: 98° C. for 10 s, 72° C. for 2 m, 25 cycles,
Step 4: 72° C. for 5 m.

The resultant product, called HYG, was verified by sequencing, as set forth in SEQ ID NO. 9.

3 PCR overlap extension to obtain a complete recombination template

The above four recovered PCR fragments, Ppox having a random mutation, SEQ ID NOs. 9, 17 and 18 were overlap-extended to obtain a homologous recombination template, which was recovered and purified. The specific method was as follows:

the fragments POX_Upstream, POX, HYG and POX_Downstream were added in equimolar amount to serve as templates, wherein the upstream and downstream primers were respectively POX_Upstream-F and POX_Downstream-R; and PCR overlap extension was performed by using PrimeSTAR® HS high-fidelity DNA polymerase.

The PCR reaction conditions were as follows:
Step 1: 98° C. for 30 s,
Step 2: 98° C. for 10 s, 50° C. for 10 s, 72° C. for 3 m, 30 cycles,
Step 3: 72° C. for 5 m.

After gel electrophoresis, a recombinant fragment having a size of about 2.6 Kb was recovered and purified.

FIG. 1 is a schematic diagram showing the integration of the POX gene with a mutation site by homologous recombination and removal of the hygromycin screening marker according to the present invention.

Example 4 Construction of *Candida tropicalis* POX Gene Mutant Library

1. Preparation of Yeast Electroporation-Competent Cells

*Candida tropicalis* CCTCC M2011192 cultured overnight on a shaker at 30° C., 250 rpm were inoculated into 100 mL of the YPD medium of Example 1 until $OD_{620}$ reached 0.1. The cells were cultured under the same conditions until $OD_{620}$ reached 1.3, and then the cells were collected by centrifugation at 3000 g and 4° C. The cells were washed twice with ice-cold sterile water and collected, then re-suspended in 10 ml of 1M sorbitol solution which was pre-cooled on ice, and then collected by centrifugation at 4° C. and 1500 g and re-suspended in 1 ml of the above sorbitol solution. Aliquots of 1004 of the cell suspension were used for genetic transformation.

2. Electroporation of Yeast Competent Cells

The above competent cells were added with 1 μg of the DNA fragment for recombination recovered in the step (3) of Example 3, and placed on ice for 5 min, then rapidly transferred to a 0.2 cm electroporation cuvette, and electroporated (BioRad, Micropulser™ Electroporator, transformation procedure SC2, 1.5 kV, 25 uFD, 200 ohms). The electroporated competent cells were quickly added with a mixture of 1 mL of YPD and 1M sorbitol (1:1, v/v), and cultured at 30° C., 200 rpm for 2 hours. The bacterial solution was collected, spread on a YPD medium plate containing 100 mg/L hygromycin B, and subjected to static culture at 30° C. for 2 to 3 days until single colonies grew.

Example 5 Screening of Mutant Strains

1 Screening method: single colonies obtained in Example 4 were selected to add in a YPD culture medium containing 100 mg/L of hygromycin B, and cultured overnight at 30° C. and 250 rpm, and colony PCR was performed to identify a positive clone with primers HYG-F and HYG-R (HYG-F: 5'-CTCGGAGGGCGAAGAATCTC-3' (SEQ ID NO.10); HYG-R: 5'-CAATGACCGCTGTTATGCGG-3' (SEQ ID NO.11)). The positive clone was inoculated into a seed medium containing 100 mg/L of hygromycin B, and cultured at 250 rpm and 30° C. until the $OD_{620}$ reached 0.8, then 3.5 mL of the seed solution was inoculated into a shake flask filled with a fermentation medium. The culturing at 250 rpm and 30° C. continued for 120 hours until the end of the fermentation. A detection sample was prepared by taking 0.5 g of fermentation broth for GC detection, and the yield of C12 dibasic acid and long-chain dibasic acid impurity of shorter carbon-chain, C10 dibasic acid, was calculated.

2 Screening results: a candidate strain with reduced content of long-chain dibasic acid impurity of shorter carbon-chain compared to the original strain CCTCC M2011192 was screened, designated as 526HYG. The acid yield and the content of C10 dibasic acid impurity were shown in Table 1.

TABLE 1

| Strain | CCTCC M2011192 | 526HYG |
|---|---|---|
| Yield of C12 dibasic acid (mg/g) | 147.9 | 149.8 |
| Mass ratio of C10 dibasic acid (%) | 0.46 | 0.27 |

The mass ratio of the C10 dibasic acid impurity was the mass percentage of the C10 dibasic acid to C12 dibasic acid.

Example 6 Sequence Analysis of POX Gene in the Mutant Strain 526HYG

1 According to the method of Example 2, the genomic DNAs of the *Candida tropicalis* CCTCC M2011192 and 526HYG were extracted, and the promoter region of POX gene was amplified by using PrimeSTAR® HS high-fidelity DNA polymerase from Tarkara company, wherein the primers were Ppox-F and Ppox-R.

The PCR reaction conditions were as follows:
Step 1: 98° C. for 30 s,
Step 2: 98° C. for 10 s, 50° C. for 10 s, 72° C. for 1 m, 30 cycles,
Step 3: 72° C. for 5 m.

2. After completion of the PCR, the product was subject to gel electrophoresis and recovered and purified.

3. Addition of As to the purified PCR fragment: 204 of recovered PCR fragment was added with 4 μL of 10× Takara Taq Buffer, 3.2 μL of dNTPs (each 10 mM) and 0.2 μL of Takara Taq, supplemented with $ddH_2O$ to 40 μL, incubated at 72° C. for 20 minutes, and recovered by Axygen PCR purification kit.

4. TA cloning. 44 of the PCR fragment recovered after addition of As were added with 14 pMD19-T vector backbone and 54 Solution I, mixed well and incubated at 16° C. for 30 min. The ligation product was transformed into DH5α chemical competent cells and positive clones were picked and sent to Majorbio(Shanghai Majorbio Bio-Pharm Technology Co., Ltd) for sequencing.

The results showed that: the sequence of the POX gene of the parental CCTCC M2011192 was identical to the sequence in the Gen BANK database (Accession Number: M12161), while the mutant strain 526HYG had a base deletion mutation in the promoter region. As shown in FIG.

2, the base mutation occurred in the promoter region of POX was indicated with black box (192 represented the parental strain CCTCC M2011192), the sequence of which was set forth in SEQ ID NO: 16.

Example 7 Removal of the Resistance Screening Marker

1. Preparation of a Homologous Recombination Template

The genomic DNA of the *Candida tropicalis* mutant strain 526HYG was used as a template to amplify recombinant template fragments POX-Upstream-2 and Ppox necessary for removal of the resistance screening marker, using PrimeSTAR® HS high-fidelity DNA polymerase, and recovered after gel electrophoresis. The sequence obtained was set forth in SEQ ID NOs. 14 and 15. The primer sequences were as follows:

```
POX_Upstream-F:
                                    (SEQ ID NO. 3)
5'-ACAACAACGAAGAAGACTCA-3'

POX_Upstream-2R:
                                    (SEQ ID NO. 12)
5'-CTGTCAAGTGCCAAATCACCCCATTTCTTCCTCCAATCA-3'

Ppox-F:
                                    (SEQ ID NO. 1)
5'-GTGATTTGGCACTTGACAG-3'

Ppox-2R:
                                    (SEQ ID NO. 13)
5'-ATGATTGATGCAGAAGCAAG-3'
```

The PCR reaction conditions were as follows:
Step 1: 98° C. for 30 s,
Step 2: 98° C. for 10 s, 50° C. for 10 s, 72° C. for 1 m, 30 cycles,
Step 3: 72° C. for 5 m.

The above PCR fragments were recovered and purified, and equimolar amounts of POX_Upstream-2 and Ppox were added as templates, with the primers POX_Upstream-F and Ppox-R. PCR overlap reaction was carried out with PrimeSTAR® HS high-fidelity DNA polymerase. The PCR conditions were as follows:
Step 1: 98° C. for 30 s
Step 2: 98° C. for 10 s, 50° C. for 10 s, 72° C. for 1 m 30 s, 30 cycles
Step 3: 72° C. for 5 m.

After gel electrophoresis, a fragment obtained by the overlap extension of about 1.3 Kb in size was recovered and purified, which is a homologous recombination template necessary for the removal of the hygromycin screening marker, and the sequence thereof was set forth in SEQ ID NO. 20.

2. Removal of the Resistance Screening Marker

Freshly competent cells of strain 526HYG for electroporation were prepared, added with 1 µg of the recovered recombinant fragment of step 1, placed on ice for 5 min, and then rapidly transferred to a 0.2 cm electroporation cuvette pre-chilled on ice, and electroporated (supra, 1.5 kV, 25 uFD, 200 ohms). The electroporated competent cells were quickly added to a mixture of 1 mL of YPD and 1M sorbitol (1:1, v/v), and cultured at 30° C., 200 rpm for 2 hours. The bacterial solution was collected, spread on a plate with the YPD medium containing no antibiotics, and subjected to static culture at 30° C. for 2 to 3 days until single colonies grew.

3. Screening of a Strain with the Resistance Marker Removed

Single colonies were picked and inoculated separately on YPD plates with or without hygromycin (100 mg/L). The single colonies that could not grow on the medium containing antibiotics but could grow on the medium containing no antibiotics were picked and inoculated in a 2 mL centrifuge tube containing 1 mL of the YPD medium, and cultured overnight at 4° C. and 250 rpm. In the next day, the strain was identified by colony PCR to determine whether the resistance screening marker was removed. The primers were as follows.

a) POX_Upstream-F and Ppox-2R
The PCR conditions were as follows:
Step 1: 98° C. for 30 s,
Step 2: 98° C. for 10 s, 50° C. for 10 s, 72° C. for 1 m 30 s, 30 cycles,
Step 3: 72° C. for 5 m.

b)
```
HYG-F:
                                    (SEQ ID NO. 22)
5'-CTCGGAGGGCGAAGAATCTC-3'

HYG-R:
                                    (SEQ ID NO. 23)
5'-CAATGACCGCTGTTATGCGG-3'
```

The PCR conditions were as follows:
Step 1: 98° C. for 30 s,
Step 2: 98° C. for 10 s, 55° C. for 30 s, 72° C. for 35 s, 30 cycles in total,
Step 3: 72° C. for 5 m.

4 Screening Results

By colony PCR, one strain with the resistance screening marker removed was screened out, and verified by sequencing that the same mutation was present in the promoter region of the POX gene in this strain as the strain 526HYG, and the hygromycin screening marker gene was removed. This strain was eventually designated as 526.

Example 8 Production of a Long-Chain Dibasic Acid by Strain 526 by Fermentation

Fermentation: Strain 526 was inoculated to a 2 ml centrifuge tube containing 1 ml of YPD medium of Example 1, and incubated at 30° C. on a shaker at 250 RPM for 1 day. The above bacterial solution was inoculated into a 500 mL shake flask with 30 ml of the seed medium of Example 1, wherein the inoculation amount was 3%, and cultured at 250 rpm and 30° C. on a shaker for 36 to 48 hours until $OD_{620}$ reached 0.8 (after 30-fold dilution). The seed solution was inoculated into a shake flask containing 15 ml of the fermentation medium of Example 1, wherein the inoculation amount was 20%, and the substrate was n-dodecane in the fermentation medium. The culturing on a shaker at 250 rpm and 30° C. was continued until the completion of the fermentation. A 0.5 g sample of the fermentation broth was taken, and the yield of C12 dibasic acid and the mass ratio of C10 dibasic acid were calculated using the method described in Example 1.4, as shown in Table 2 below.

TABLE 2

| Strain | CCTCC M2011192 | 526 |
|---|---|---|
| Yield of C12 dibasic acid (mg/g) | 148.2 | 150.3 |

TABLE 2-continued

| Strain | CCTCC M2011192 | 526 |
|---|---|---|
| Mass ratio of C10 dibasic acid (%) | 0.48 | 0.25 |

The mass ratio of C10 dibasic acid in the present invention is mass percentage of C10 dibasic acid to C12 dibasic acid. As shown in Table 2, the mass ratio of C10 dibasic acid was decreased by 47.9%.

Extraction and Purification:

(1) The above fermentation broth was adjusted to have a pH of 8.5 with a sodium hydroxide solution with a mass concentration of 30%, added with water until the concentration of the long-chain dibasic acid was 6 wt %, heated to 45° C., and filtered with a ceramic membrane having a pore size of 0.05 μm [purchased from Suntar Membrane Technology (Xiamen) Co., Ltd.]. The ceramic membrane used had a membrane area of 0.84 m² and a pre-membrane pressure of 0.3 MPa. The membrane clear liquid was collected.

(2) The collected membrane clear liquid was decolorized by adding 5 wt % of powdered activated carbon (relative to the amount of the long-chain dibasic acid contained in the solution) at 60° C., and filtered to obtain a clear liquid.

(3) The clear liquid was further added with sulfuric acid to adjust the pH to 3, cooled to 30° C., and filtered to obtain a wet solid. The wet solid was washed with purified water 5 times the weight of the wet solid, filtered and then dried to obtain the primary product of C12 dibasic acid.

(4) The primary product of C12 dibasic acid was added with acetic acid at a concentration of 97% of 3.5 times the amount (relative to the weight of the primary product of C12 dibasic acid), heated to 85° C. for dissolution, added with 1% macroporous powdered activated carbon (relative to the weight of the primary product of C12 dibasic acid) for decoloration, kept at 85° C. for 1 hour, and hot filtered to obtain a clear liquid. The solution was cooled to 30° C. at a rate of 10° C./hour, and C12 long-chain dibasic acid crystal solution was obtained, which was filtered to obtain a wet solid which was to be washed with water to remove the solvent, and dried to obtain the secondary product of C12 dibasic acid.

Purity of C12 dibasic acid as well as the content of C10 dibasic acid impurity in the primary and secondary products of dibasic acid obtained in the extraction and purification steps (3) and (4) were determined and calculated by using the method as described in Example 1.4, as shown in Table 3 below:

TABLE 3

| | Strain | CCTCC M2011192 | 526 |
|---|---|---|---|
| Primary product of C12 dibasic acid | Purity of C12 dibasic acid (%) | 99.3 | 99.6 |
| | Content of C10 dibasic acid (ppm) | 1120 | 440 |
| Secondary product of C12 dibasic acid | Purity of C12 dibasic acid (%) | 99.4 | 99.8 |
| | Content of C10 dibasic acid (ppm) | 450 | 180 |

As shown in the Table 3, after the extraction and purification of C10 dibasic acid impurity in the C12 dibasic acid product, the purity of the fermentation product, the long-chain dibasic acid, was further increased, and the content of the long chain dibasic acid impurity of shorter carbon-chain was decreased, and the difficulty of subsequent extraction and purification processes was reduced.

Example 9

To further verify the mutation above, the genome DNA of the yeast 526HYG was extracted, and a DNA fragment comprising the mutated POX promoter and the HYG resistance gene was amplified by PCR with the PrimeSTAR® HS high-fidelity DNA polymerase, wherein the PCR reaction conditions were the same as those in Example 3.3. The fragment of about 2.7 Kb in size was recovered and purified after gel electrophoresis, and confirmed by sequencing, the sequence of which was set forth in SEQ ID NO.21.

The yeast homologous recombination method was the same as that in Examples 4 and 5, and colony PCR for identification was the same as that in Example 7.3, with the primers HYG-F (SEQ ID NO.22) and HYG-R (SEQ ID NO.23). The screened positive clone was named as 527 HYG, and the sequencing method of the POX promoter was the same as that in Example 6. By sequencing, it was verified that the mutation in the POX4 promoter was the same as that of the strain 526.

The methods for fermentation and determination of dibasic acid were the same as those in Example 5.1. The results were shown in Table 4. Compared with control strain CCTCC M2011192, the contents of C10 dibasic acid impurity in the screened strains 527HYG and 526HYG were respectively significantly decreased.

TABLE 4

| Strain | CCTCC M2011192 | 526HYG | 527HYG |
|---|---|---|---|
| Yield of C12 dibasic acid (mg/g) | 151.7 | 148.0 | 147.2 |
| Mass ratio of C10 dibasic acid (%) | 0.47 | 0.28 | 0.29 |

Example 10

The DNA fragment (SEQ ID NO: 21) in Example 9 was introduced into *Candida tropicalis* (CCTCC M 203052) by homologous recombination according to the method as described in Examples 4 and 5. The method of sequencing the promoter sequence of the gene POX of the obtained single colony and the parent strain (CCTCC M 203052) were the same as described in Example 6. By sequencing, it was confirmed that the sequence of the gene POX in the parent strain (CCTCC M 203052) was consistent with the published sequence in GenBank with the Accession Number of M12161, while the screened out colony carried a mutation in this gene in which the mutation was consistent with SEQ ID NO:16. One strain was designated as 528HYG.

The method for fermentation was according to Example 5, in which the strains used were CCTCC M 203052 and 528HYG. After completion of fermentation, a sample of 0.5 g of each fermentation broth was collected and the yield of C12 dibasic acid and the amount of C10 dibasic acid impurity were calculated, as shown in Table 5. The results indicated that the content of C10 dibasic acid impurity in the fermentation broth by the strain 528HYG was significantly reduced compared the parent strain CCTCC M 203052.

TABLE 5

| Strain | CCTCC M203052 | 528HYG |
|---|---|---|
| Yield of C12 dibasic acid (mg/g) | 132.1 | 133.6 |
| Mass ratio of C10 dibasic acid (%) | 0.44 | 0.19 |

The invention claimed is:

1. An isolated mutated POX gene or a variant thereof, wherein said isolated mutated POX gene or a variant thereof comprises

[i] a nucleic acid sequence having at least 80% sequence identity to SEQ ID NO: 24, and

[ii] a deletion of any one nucleotide base in the promoter of said POX gene from nucleic acid residues 266-275 of SEQ ID NO: 24.

2. The isolated mutated POX gene or a variant thereof of claim 1, wherein the isolated mutated POX gene or a variant thereof comprises

[a] a nucleic acid sequence as set forth in SEQ ID NO: 27 or 29, or

[b] a nucleic acid sequence having at least 85%, 90%, 91% 92%, 93%, 94%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95% or 99.96% sequence identity to SEQ ID NO: 24.

3. A microorganism comprising the isolated mutated POX gene or a variant thereof of claim 1, wherein the microorganism is selected from the group consisting of (i) *Corynebacterium, Geotrichum candidum, Candida, Pichia, Rhodotroula, Saccharomyces* and *Yarrowia*; (ii) yeast; or (iii) *Candida tropicalis* or *Candida sake.*

* * * * *

SEQUENCE LISTING

<160> NUMBER OF SEQ ID NOS: 29

<210> SEQ ID NO 1
<211> LENGTH: 19
<212> TYPE: DNA
<213> ORGANISM: Artificial Sequence
<220> FEATURE:
<223> OTHER INFORMATION: primer Ppox-F

<400> SEQUENCE: 1
gtgatttggc acttgacag                                                    19

<210> SEQ ID NO 2
<211> LENGTH: 20
<212> TYPE: DNA
<213> ORGANISM: Artificial Sequence
<220> FEATURE:
<223> OTHER INFORMATION: primer Ppox-R

<400> SEQUENCE: 2
ttttgaagtt cggtaggcat                                                   20

<210> SEQ ID NO 3
<211> LENGTH: 20
<212> TYPE: DNA
<213> ORGANISM: Artificial Sequence
<220> FEATURE:
<223> OTHER INFORMATION: primer POX_Upstream-F

<400> SEQUENCE: 3
acaacaacga agaagactca                                                   20

<210> SEQ ID NO 4
<211> LENGTH: 20
<212> TYPE: DNA
<213> ORGANISM: Artificial Sequence
<220> FEATURE:
<223> OTHER INFORMATION: primer POX_Upstream-R

<400> SEQUENCE: 4
cccatttctt cctccaatca                                                   20

<210> SEQ ID NO 5
<211> LENGTH: 20
<212> TYPE: DNA
<213> ORGANISM: Artificial Sequence
<220> FEATURE:
<223> OTHER INFORMATION: primer POX_Downstream-F

<400> SEQUENCE: 5
atgcctaccg aacttcaaaa                                                   20

<210> SEQ ID NO 6
<211> LENGTH: 20
<212> TYPE: DNA
<213> ORGANISM: Artificial Sequence
<220> FEATURE:
<223> OTHER INFORMATION: primer POX_Downstream-R

<400> SEQUENCE: 6
tctttgttgg tctttggtca                                                   20

<210> SEQ ID NO 7
<211> LENGTH: 40
<212> TYPE: DNA
<213> ORGANISM: Artificial Sequence

```
<220> FEATURE:
<223> OTHER INFORMATION: primer POX_HYG-F

<400> SEQUENCE: 7
tgattggagg aagaaatggg gcatgcgaac ccgaaaatgg                          40

<210> SEQ ID NO 8
<211> LENGTH: 39
<212> TYPE: DNA
<213> ORGANISM: Artificial Sequence
<220> FEATURE:
<223> OTHER INFORMATION: primer POX_HYG-R

<400> SEQUENCE: 8
ctgtcaagtg ccaaatcacg ctagcagctg gatttcact                           39

<210> SEQ ID NO 9
<211> LENGTH: 1775
<212> TYPE: DNA
<213> ORGANISM: Artificial Sequence
<220> FEATURE:
<223> OTHER INFORMATION: HYG

<400> SEQUENCE: 9
tgattggagg aagaaatggg gcatgcgaac ccgaaaatgg agcaatcttc cccggggcct    60
ccaaatacca actcacccga gagagataaa gagacaccac ccaccacgag acggagtata   120
tccaccaagg taagtaactc agagttaatg atacaggtgt acacagctcc ttccctagcc   180
attgagtggg tatcacatga cactggtagg ttacaaccac gtttagtagt tattttgtgc   240
aattccatgg ggatcaggaa gtttggtttg gtgggtgcgt ctactgattc ccctttgtct   300
ctgaaaatct tttccctagt ggaacacttt ggctgaatga tataaattca ccttgattcc   360
caccctccct tctttctctc tctctctgtt acacccaatt gaattttctt tttttttta    420 ctttccctcc ttctttatca tcaaagataa gtaagtttat caattgccta ttcagaatga   480
aaaagcctga actcaccgcg acgtctgtcg agaagtttct catcgaaaag ttcgacagcg   540
tctccgacct catgcagctc tcggagggcg aagaatctcg tgctttcagc ttcgatgtag   600
gagggcgtgg atatgtcctc cgggtaaata gctgcgccga tggtttctac aaagatcgtt   660
atgtttatcg gcactttgca tcggccgcgc tcccgattcc ggaagtgctt gacattgggg   720
aattcagcga gagcctcacc tattgcatct cccgccgtgc acagggtgtc acgttgcaag   780 acctcctga aaccgaactc cccgctgttc tccagccggt cgcggaggcc atggatgcga   840
tcgctgcggc cgatcttagc cagacgagcg ggttcggccc attcggaccg caaggaatcg   900
gtcaatacac tacatggcgt gatttcatat gcgcgattgc tgatccccat gtgtatcact   960
ggcaaactgt gatggacgac accgtcagtg cgtccgtcgc gcaggctctc gatgagctca  1020
tgctttgggc cgaggactgc cccgaagtcc ggcacctcgt gcacgcggat ttcggctcca  1080
acaatgtcct cacggacaat ggccgcataa cagcggtcat tgactggagc gaggcgatgt  1140
tcggggattc ccaatacgag gtcgccaaca tcttcttctg gaggccgtgg ttggcttgta  1200
tggagcagca gacgcgctac ttcgagcgga ggcatccgga gcttgcagga tcgccgcggc  1260
tccgggcgta tatgctccgc attggtcttg accaactcta tcagagcttg gttgacggca  1320
atttcgatga tgcagcttgg gcgcagggtc gatgcgacga atcgtccga tccggagccg  1380 ggactgtcgg gcgtacacaa atcgcccgca gaagcgcggc cgtctggacc gatggctgtg  1440
tagaagtact cgccgatagt ggaaaccgac gccccagcac tcgtccgagg gcaaaggaat  1500
```

-continued

| | | |
|---|---|---|
| agtgtgctac ccacgcttac tccaccagag ctattaacat cagaaatatt tattctaata | 1560 | |
| aataggatgc aaaaaaaaaa ccccccttaa taaaaaaaaa agaaacgatt ttttatctaa | 1620 | |
| tgaagtctat gtatctaaca aatgtatgta tcaatgttta ttccgttaaa caaaaatcag | 1680 | |
| tctgtaaaaa aggttctaaa taaatattct gtctagtgta cacattctcc caaaatagtg | 1740 | |
| aaatccagct gctagcgtga tttggcactt gacag | 1775 | |

<210> SEQ ID NO 10
<211> LENGTH: 20
<212> TYPE: DNA
<213> ORGANISM: Artificial Sequence
<220> FEATURE:
<223> OTHER INFORMATION: primer HYG-F

<400> SEQUENCE: 10
ctcggagggc gaagaatctc                                                20

<210> SEQ ID NO 11
<211> LENGTH: 20
<212> TYPE: DNA
<213> ORGANISM: Artificial Sequence
<220> FEATURE:
<223> OTHER INFORMATION: primer HYG-R

<400> SEQUENCE: 11
caatgaccgc tgttatgcgg                                                20

<210> SEQ ID NO 12
<211> LENGTH: 39
<212> TYPE: DNA
<213> ORGANISM: Artificial Sequence
<220> FEATURE:
<223> OTHER INFORMATION: primer POX_Upstream-2R

<400> SEQUENCE: 12
ctgtcaagtg ccaaatcacc ccatttcttc ctccaatca                           39

<210> SEQ ID NO 13
<211> LENGTH: 18
<212> TYPE: DNA
<213> ORGANISM: Artificial Sequence
<220> FEATURE:
<223> OTHER INFORMATION: primer Ppox-2R

<400> SEQUENCE: 13
ggaaccgagg ccaaatta                                                  18

<210> SEQ ID NO 14
<211> LENGTH: 267
<212> TYPE: DNA
<213> ORGANISM: Artificial Sequence
<220> FEATURE:
<223> OTHER INFORMATION: POX-Upstream-2

<400> SEQUENCE: 14
acaacaacga agaagactca ggacacttta gtttattctg tttcttttt tgcaactccg      60 ctgggaataa tgaagcaccc gggcgatggc aatctcgcat ataagtttcg gagtttttc     120 tagaaggaat tgcctctct acgtcacgta ccccgatgtt tgtcccacgg tttatcatcc    180
agcgggaaga aagagataat cacaggggta gagaccttgg ttatgggctg attggaggaa   240
gaaatggggt gatttggcac ttgacag                                       267

<210> SEQ ID NO 15
<211> LENGTH: 423
<212> TYPE: DNA
<213> ORGANISM: Artificial Sequence
<220> FEATURE:
<223> OTHER INFORMATION: Ppox

<400> SEQUENCE: 15

```
gtgatttggc acttgacagc gcgagagtgg ttaacacctg gtttccctca tttgggttct      60
gacatttgat aagttgaaag aacaatgcag aattcacatg gctaatttgg cctcggttcc     120
acaacgcact cagcattaaa aaaaaaatac gcaatggcag ctcggtcgac gcagcagaag     180
cgccgacgta ccgtcgcgtt gccccgccca tgcctcgccg acccctccac cgccatcgtt     240
tgcccattgt ttgtggtagt gcgccgtgac acaaaaactt gtcctgtcac atgctgaagt     300
tacaccaaca taactactat gggattacgt aatcaaaaat ttcacagttt taacaaaaaa     360
aaatcataca atcaacattg ggacatcttg ccctccccca caaaacttgc ttctgcatca     420
atc                                                                   423
```

<210> SEQ ID NO 16
<211> LENGTH: 544
<212> TYPE: DNA
<213> ORGANISM: Artificial Sequence
<220> FEATURE:
<223> OTHER INFORMATION: mutated POX

<400> SEQUENCE: 16

```
gtgatttggc acttgacagc gcgagagtgg ttaacacctg gtttccctca tttgggttct      60
gacatttgat aagttgaaag aacaatgcag aattcacatg gctaatttgg cctcggttcc     120
acaacgcact cagcattaaa aaaaaaatac gcaatggcag ctcggtcgac gcagcagaag     180
cgccgacgta ccgtcgcgtt gccccgccca tgcctcgccg acccctccac cgccatcgtt     240
tgcccattgt ttgtggtagt gcgccgtgac acaaaaactt gtcctgtcac atgctgaagt     300
tacaccaaca taactactat gggattacgt aatcaaaaat ttcacagttt taacaaaaaa     360
aaatcataca atcaacattg ggacatcttg ccctccccca caaaacttgc ttctgcatca     420
atcatatata aacatcatga ataagccta aactcacttc ttttttttc atccttccta     480
cttcttcttt catagtaact acttttttttt tattaccaca cttattcatt cataccacgc     540
tatc                                                                  544
```

<210> SEQ ID NO 17
<211> LENGTH: 248
<212> TYPE: DNA
<213> ORGANISM: Artificial Sequence
<220> FEATURE:
<223> OTHER INFORMATION: POX_Upstream

<400> SEQUENCE: 17

```
acaacaacga agaagactca ggacacttta gtttattctg tttcttttt tgcaactccg      60
ctgggaataa tgaagcaccc gggcgatggc aatctcgcat ataagtttcg gagttttttc    120
tagaaggaat ttgcctctct acgtcacgta ccccgatgtt tgtcccacgg tttatcatcc    180
agcgggaaga aagagataat cacaggggta gagaccttgg ttatgggctg attggaggaa    240
gaaatggg                                                              248
```

<210> SEQ ID NO 18
<211> LENGTH: 183
<212> TYPE: DNA
<213> ORGANISM: Artificial Sequence
<220> FEATURE:
<223> OTHER INFORMATION: POX_Downstream

<400> SEQUENCE: 18

```
atgcctaccg aacttcaaaa agaaagagaa ctcaccaagt tcaacccaaa ggagttgaac      60
tacttcttgg aaggttccca agaaagatcc gagatcatca gcaacatggt cgaacaaatg     120
caaaaagacc ctatcttgaa ggtcgacgct tcatactaca acttgaccaa agaccaacaa     180
aga                                                                   183
```

<210> SEQ ID NO 19
<211> LENGTH: 5873
<212> TYPE: DNA
<213> ORGANISM: Artificial Sequence
<220> FEATURE:
<223> OTHER INFORMATION: vector pCIB2

<400> SEQUENCE: 19

```
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg aattcggtct     240
agtatgattg tcaataatga tgggtcatcg tttcctgatt cgacgttccc tgtggtgtcg     300
ttaaatagcc tgtctgaaat ctcctccatg attgtgttgg tgtgtgttgt ttgactttcc     360
caattgctta catttttttc ttcaaggatt cgctccaaaa tagacagaaa ttatcgcgac     420
aagtcagacg aacgtcgcac gaggcgaacc aaattcttta gaagcatacg aaaactcact     480
ttatttccat tagaagtatt aaattaacaa atatataata tacaggatac aaagtaaaag     540
cacgcttaag caaccaaagc ggaagcggta gcggattcgt atttccagtt aggtggcaag     600
acagcgacgg ttctgtagta tctggccaat ctgtggattc tagattcaat caaaatcaat     660
ctgaacttgg agtccttgtc cttctctgttt cttccaagt gctttctgac agagacagcc     720
ttcttgatca gtagtacaa gtcttctggg atttctggag ccaaaccgtt ggatttcaag     780
attctcaaga tcttgttacc agtgacaacc ttggcttggg aaacaccgtg agcatctctc     840
aagataacac caatttgaga tggagtcaaa cccttctgg cgtacttgat gacttgttca     900
acaacttcgt cagaagacaa cttgaaccaa gatggagcgt tcttgagta tggaagagcg     960 gaggaggaaa taccttacc ctaaaataac aagagctaat gttagtaatt tgaaaaaaaa    1020
gacgttgagc acgcacaccc catccacccc acaggtgaaa cacatcaaac gtagcaagaa    1080
caatagttgg ccctcccgtc aagggggcag gtaattgtcc aagtacttta gaaaagtatg    1140
tttttaccca taagatgaac acacacaaac cagcaaaagt atcaccttct gcttttcttg    1200
gttgaggttc aaattatgtt tggcaataat gcagcgacaa tttcaagtac ctaaagcgta    1260
tatagtaaca attctaggtc tgtatagtcg accgtaggtg aatcgtttac tttaggcaag    1320
accttgtccc tgataaagcc aggttgtact ttctattcat tgagtgtcgt ggtggtggta    1380
gtggtggttg attgggctgt tgtggtagta gtagtggttg tgatttggaa catacagatg    1440
aatgcatacg acccatgatg actgattcgt ttctttattg agttgatggt aagaaagaga    1500
agaagaggag gtaaaaaggt ggtagagtga aaaattttt tctcttaaaa gtgagagaga    1560
```

-continued

```
gaaagagaaa aatttcactg cgaaacaaat ggttgggac acgacttttt tcaggaattt      1620
ttactcgaag cgtatatgca ggaaagttgt tgttagggaa tatggagcca caagagagct    1680
gcgaattcga gctcggtacc cggggatcct ctagagtcga cctgcaggca tgcgaacccg    1740
aaaatggagc aatcttcccc ggggcctcca aataccaact cacccgagag agagaaagag   1800
acaccaccca ccacgagacg gagtatatcc accaaggtaa gtaactcagg gttaatgata   1860
caggtgtaca cagctccttc cctagccatt gagtgggtat cacatgacac tggtaggtta   1920
caaccacgtt tagtagttat tttgtgcaat tccatgggga tcaggaagtt tggtttggtg   1980
ggtgcgtcta ctgattcccc tttgtctctg aaaatctttt ccctagtgga acactttggc   2040
tgaatgatat aaattcacct tgattcccac cctcccttct ttctctctct ctctgttaca   2100
cccaattgaa ttttcttttt tttttactt tccctccttc tttatcatca aagataagta    2160
agtttatcaa ttgcctattc agaatgaaaa agcctgaact caccgcgacg tctgtcgaga   2220
agtttctcat cgaaaagttc gacagcgtct ccgacctcat gcagctctcg gagggcgaag   2280
aatctcgtgc tttcagcttc gatgtaggag ggcgtggata tgtcctccgg gtaaatagct   2340
gcgccgatgg tttctacaaa gatcgttatg tttatcggca ctttgcatcg gccgcgctcc   2400
cgattccgga agtgcttgac attggggaat tcagcgagag cctcacctat gcatctccc    2460
gccgtgcaca gggtgtcacg ttgcaagacc tccctgaaac cgaactcccc gctgttctcc   2520
agccggtcgc ggaggccatg gatgcgatcg ctgcggccga tcttagccag acgagcgggt   2580
tcggcccatt cggaccgcaa ggaatcggtc aatacactac atggcgtgat ttcatatgcg   2640
cgattgctga tccccatgtg tatcactggc aaactgtgat ggacgacacc gtcagtgcgt   2700
ccgtcgcgca ggctctcgat gagctcatgc tttgggccga ggactgcccc gaagtccggc   2760
acctcgtgca cgcggatttc ggctccaaca atgtcctcac ggacaatggc cgcataacag   2820
cggtcattga ctggagcgag gcgatgttcg gggattccca atacgaggtc gccaacatct   2880
tcttctggag gccgtggttg gcttgtatgg agcagcagac gcgctacttc gagcggaggc   2940
atccggagct tgcaggatcg ccgcggctcc gggcgtatat gctccgcatt ggtcttgacc   3000
aactctatca gagcttggtt gacggcaatt tcgatgatgc agcttgggcg cagggtcgat   3060
gcgacgcaat cgtccgatcc ggagccggga ctgtcgggcg tacacaaatc gcccgcagaa   3120
gcgcggccgt ctggaccgat ggctgtgtag aagtactcgc cgatagtgga aaccgacgcc   3180
ccagcactcg tccgagggca aggaatagt gtgctaccca cgcttactcc accagagcta    3240
ttaacatcag aaatatttat tctaataaat aggatgcaaa aaaaaaccc cccttaataa    3300
aaaaaaaga aacgattttt tatctaatga agtctatgta tctaacaaat gtatgtatca    3360
atgtttattc cgttaaacaa aaatcagtct gtaaaaaagg ttctaaataa atattctgtc   3420
tagtgtacac attctcccaa aatagtgaaa tccagctgct agcgtgtaag cttggcactg   3480
gccgtcgttt tacaacgtcg tgactgggaa accctggcg ttacccaact taatcgcctt    3540
gcagcacatc ccccttcgc cagctggcgt aatagcgaag aggcccgcac cgatcgccct    3600
tcccaacagt tgcgcagcct gaatggcgaa tggcgcctga tgcggtattt tctccttacg   3660
catctgtgcg gtatttcaca ccgcatatgg tgcactctca gtacaatctg ctctgatgcc   3720
gcatagttaa gccagccccg acacccgcca acacccgctg acgcgccctg acgggcttgt   3780
ctgctcccgg catccgctta cagacaagct gtgaccgtct ccgggagctg catgtgtcag   3840
aggttttcac cgtcatcacc gaaacgcgcg agacgaaagg gcctcgtgat acgcctattt   3900
ttataggtta atgtcatgat aataatggtt tcttagacgt caggtggcac ttttcgggga   3960
```

| | | | | |
|---|---|---|---|---|
| aatgtgcgcg | gaacccctat | ttgtttattt | ttctaaatac | attcaaatat gtatccgctc | 4020 |
| atgagacaat | aaccctgata | aatgcttcaa | taatattgaa | aaaggaagag tatgagtatt | 4080 |
| caacatttcc | gtgtcgccct | tattcccttt | tttgcggcat | tttgccttcc tgttttgct | 4140 |
| cacccagaaa | cgctggtgaa | agtaaaagat | gctgaagatc | agttgggtgc acagtgggt | 4200 |
| tacatcgaac | tggatctcaa | cagcggtaag | atccttgaga | gttttcgccc cgaagaacgt | 4260 |
| tttccaatga | tgagcacttt | taaagttctg | ctatgtggcg | cggtattatc ccgtattgac | 4320 |
| gccgggcaag | agcaactcgg | tcgccgcata | cactattctc | agaatgactt ggttgagtac | 4380 |
| tcaccagtca | cagaaaagca | tcttacggat | ggcatgacag | taagagaatt atgcagtgct | 4440 |
| gccataacca | tgagtgataa | cactgcggcc | aacttacttc | tgacaacgat cggaggaccg | 4500 |
| aaggagctaa | ccgcttttt | gcacaacatg | ggggatcatg | taactcgcct tgatcgttgg | 4560 |
| gaaccggagc | tgaatgaagc | cataccaaac | gacgagcgtg | acaccacgat gcctgtagca | 4620 |
| atggcaacaa | cgttgcgcaa | actattaact | ggcgaactac | ttactctagc ttcccggcaa | 4680 |
| caattaatag | actggatgga | ggcggataaa | gttgcaggac | cacttctgcg ctcggccctt | 4740 |
| ccggctggct | ggtttattgc | tgataaatct | ggagccggtg | agcgtgggtc tcgcggtatc | 4800 |
| attgcagcac | tggggccaga | tggtaagccc | tcccgtatcg | tagttatcta cacgacgggg | 4860 |
| agtcaggcaa | ctatgatga | acgaaataga | cagatcgctg | agataggtgc ctcactgatt | 4920 |
| aagcattggt | aactgtcaga | ccaagtttac | tcatatatac | tttagattga tttaaaactt | 4980 |
| catttttaat | ttaaaaggat | ctaggtgaag | atcctttttg | ataatctcat gaccaaaatc | 5040 |
| ccttaacgtg | agttttcgtt | ccactgagcg | tcagaccccg | tagaaaagat caaaggatct | 5100 |
| tcttgagatc | ctttttttct | gcgcgtaatc | tgctgcttgc | aaacaaaaaa accaccgcta | 5160 |
| ccagcggtgg | tttgtttgcc | ggatcaagag | ctaccaactc | tttttccgaa ggtaactggc | 5220 |
| ttcagcagag | cgcagatacc | aaatactgtc | cttctagtgt | agccgtagtt aggccaccac | 5280 |
| ttcaagaact | ctgtagcacc | gcctacatac | ctcgctctgc | taatcctgtt accagtggct | 5340 |
| gctgccagtg | gcgataagtc | gtgtcttacc | gggttggact | caagacgata gttaccggat | 5400 |
| aaggcgcagc | ggtcgggctg | aacggggggt | tcgtgcacac | agcccagctt ggagcgaacg | 5460 |
| acctacaccg | aactgagata | cctacagcgt | gagctatgag | aaagcgccac gcttcccgaa | 5520 |
| gggagaaagg | cggacaggta | tccggtaagc | ggcagggtcg | gaacaggaga gcgcacgagg | 5580 |
| gagcttccag | ggggaaacgc | ctggtatctt | tatagtcctg | tcgggtttcg ccacctctga | 5640 |
| cttgagcgtc | gatttttgtg | atgctcgtca | ggggggcgga | gcctatggaa aaacgccagc | 5700 |
| aacgcggcct | ttttacggtt | cctggccttt | tgctggcctt | ttgctcacat gttctttcct | 5760 |
| gcgttatccc | ctgattctgt | ggataaccgt | attaccgcct | ttgagtgagc tgataccgct | 5820 |
| cgccgcagcc | gaacgaccga | gcgcagcgag | tcagtgagcg | aggaagcgga aga | 5873 |

<210> SEQ ID NO 20
<211> LENGTH: 673
<212> TYPE: DNA
<213> ORGANISM: Artificial Sequence
<220> FEATURE:
<223> OTHER INFORMATION: homologous recombination template for removing
      resistance marker

<400> SEQUENCE: 20

| | | | | |
|---|---|---|---|---|
| acaacaacga | agaagactca | ggacactta | gtttattctg | tttctttttt tgcaactccg | 60 |
| ctgggaataa | tgaagcaccc | gggcgatggc | aatctcgcat | ataagtttcg gagtttttc | 120 |

```
tagaaggaat tgcctctct acgtcacgta ccccgatgtt tgtcccacgg tttatcatcc      180
agcgggaaga aagagataat cacaggggta gagaccttgg ttatgggctg attggaggaa      240 gaaatgggt  gatttggcac ttgacagcgc gagagtggtt aacacctggt ttccctcatt      300
tgggttctga catttgataa gttgaaagaa caatgcagaa ttcacatggc taatttggcc      360
tcggttccac aacgcactca gcattaaaaa aaaaatacgc aatggcagct cggtcgacgc      420
agcagaagcg ccgacgtacc gtcgcgttgc cccgcccatg cctcgccgac ccctccaccg      480
ccatcgtttg cccattgttt gtggtagtgc gccgtgacac aaaaacttgt cctgtcacat      540
gctgaagtta caccaacata actactatgg gattacgtaa tcaaaaattt cacagttta      600 acaaaaaaaa atcatacaat caacattggg acatcttgcc ctcccccaca aaacttgctt      660
ctgcatcaat cat                                                         673

<210> SEQ ID NO 21
<211> LENGTH: 2711
<212> TYPE: DNA
<213> ORGANISM: Artificial Sequence
<220> FEATURE:
<223> OTHER INFORMATION: DNA fragment containing mutated POX promoter
      and HYG resistance gene

<400> SEQUENCE: 21
acaacaacga agaagactca ggacacttta gtttattctg tttctttttt tgcaactccg       60
ctgggaataa tgaagcaccc gggcgatggc aatctcgcat ataagtttcg gagtttttc      120 tagaaggaat ttgcctctct acgtcacgta ccccgatgtt tgtcccacgg tttatcatcc      180
agcgggaaga aagagataat cacaggggta gagaccttgg ttatgggctg attggaggaa      240 gaaatgggc  atgcgaaccc gaaaatggag caatcttccc cggggcctcc aaataccaac      300
tcacccgaga gagataaaga gacaccaccc accacgagac ggagtatatc caccaaggta      360
agtaactcag agttaatgat acaggtgtac acagctcctt ccctagccat tgagtgggta      420
tcacatgaca ctggtaggtt acaaccacgt ttagtagtta ttttgtgcaa ttccatgggg      480
atcaggaagt ttggtttggt gggtgcgtct actgattccc ctttgtctct gaaaatcttt      540
tccctagtgg aacactttgg ctgaatgata taaattcacc ttgattccca ccctcccttc      600
tttctctctc tctctgttac acccaattga attttctttt tttttttact ttccctcctt      660
ctttatcatc aaagataagt aagtttatca attgcctatt cagaatgaaa aagcctgaac      720
tcaccgcgac gtctgtcgag aagtttctca tcgaaaagtt cgacagcgtc tccgacctca      780
tgcagctctc ggagggcgaa gaatctcgtg ctttcagctt cgatgtagga gggcgtggat      840
atgtcctccg ggtaaatagc tgcgccgatg gtttctacaa agatcgttat gtttatcggc      900
actttgcatc ggccgcgctc ccgattccgg aagtgcttga cattggggaa ttcagcgaga      960
gcctcaccta ttgcatctcc cgccgtgcac agggtgtcac gttgcaagac ctccctgaaa     1020
ccgaactccc cgctgttctc cagccggtcg cggaggccat ggatgcgatc gctgcggccg     1080
atcttagcca gacgagcggg ttcggcccat tcggaccgca aggaatcggt caatacacta     1140
catggcgtga tttcatatgc gcgattgctg atccccatgt gtatcactgg caaactgtga     1200
tggacgacac cgtcagtgcg tccgtcgcgc aggctctcga tgagctcatg ctttgggccg     1260
aggactgccc cgaagtccgg cacctcgtgc acgcggattt cggctccaac aatgtcctca     1320
cggacaatgg ccgcataaca gcggtcattg actggagcga ggcgatgttc gggattccc      1380 aatacgaggt cgccaacatc ttcttctgga ggccgtggtt ggcttgtatg gagcagcaga     1440
```

```
cgcgctactt cgagcggagg catccggagc ttgcaggatc gccgcggctc cgggcgtata    1500
tgctccgcat tggtcttgac caactctatc agagcttggt tgacggcaat ttcgatgatg    1560
cagcttgggc gcagggtcga tgcgacgcaa tcgtccgatc cggagccggg actgtcgggc    1620
gtacacaaat cgcccgcaga agcgcggccg tctggaccga tggctgtgta aagtactcg    1680 ccgatagtgg aaaccgacgc cccagcactc gtccgagggc aaaggaatag tgtgctaccc    1740
acgcttactc caccagagct attaacatca gaaatattta ttctaataaa taggatgcaa    1800
aaaaaaaacc cccttaata aaaaaaaaag aaacgatttt ttatctaatg aagtctatgt     1860
atctaacaaa tgtatgtatc aatgtttatt ccgttaaaca aaaatcagtc tgtaaaaaag    1920
gttctaaata aatattctgt ctagtgtaca cattctccca aaatagtgaa atccagctgc    1980
tagcgtgatt tggcacttga cagcgcgaga gtggttaaca cctggtttcc ctcatttggg    2040
ttctgacatt tgataagttg aaagaacaat gcagaattca catggctaat ttggcctcgg    2100
ttccacaacg cactcagcat taaaaaaaaa atacgcaatg gcagctcggt cgacgcagca    2160
gaagcgccga cgtaccgtcg cgttgccccg cccatgcctc gccgaccct ccaccgccat     2220 cgtttgccca ttgtttgtgg tagtgcgccg tgacacaaaa acttgtcctg tcacatgctg    2280
aagttacacc aacataacta ctatgggatt acgtaatcaa aaatttcaca gttttaacaa    2340
aaaaaaatca taatcaac attgggacat cttgccctcc cccacaaaac ttgcttctgc       2400
atcaatcata tataaacatc atgaaataag cctaaactca cttctttttt tttcatcctt    2460
cctacttctt ctttcatagt aactactttt tttttattac cacacttatt cattcatacc    2520
acgctatcat gcctaccgaa cttcaaaaag aaagagaact caccaagttc aacccaaagg    2580
agttgaacta cttcttggaa ggttcccaag aaagatccga gatcatcagc aacatggtcg    2640
aacaaatgca aaaagaccct atcttgaagg tcgacgcttc atactacaac ttgaccaaag    2700
accaacaaag a                                                         2711

<210> SEQ ID NO 22
<211> LENGTH: 20
<212> TYPE: DNA
<213> ORGANISM: Artificial Sequence
<220> FEATURE:
<223> OTHER INFORMATION: primer HYG-F

<400> SEQUENCE: 22
ctcggagggc gaagaatctc                                                 20

<210> SEQ ID NO 23
<211> LENGTH: 20
<212> TYPE: DNA
<213> ORGANISM: Artificial Sequence
<220> FEATURE:
<223> OTHER INFORMATION: primer HYG-R

<400> SEQUENCE: 23
caatgaccgc tgttatgcgg                                                 20

<210> SEQ ID NO 24
<211> LENGTH: 2624
<212> TYPE: DNA
<213> ORGANISM: Candida tropicalis

<400> SEQUENCE: 24
gaattcacat ggctaatttg gcctcggttc cacaacgcac tcagcattaa aaaaaaaata    60
cgcaatggca gctcggtcga cgcagcagaa gcgccgacgt accgtcgcgt tgccccgccc    120
```

```
atgcctcgcc gacccctcca ccgccatcgt ttgcccattg tttgtggtag tgcgccgtga    180
cacaaaaact tgtcctgtca catgctgaag ttacaccaac ataactacta tgggattacg    240
taatcaaaaa tttcacagtt ttaacaaaaa aaaatcata caatcaacat tgggacatct     300
tgccctcccc cacaaaactt gcttctgcat caatcatata taaacatcat gaaataagcc    360
taaactcact tctttttttt tcatccttcc tacttcttct ttcatagtaa ctacttttt     420 tttattacca cacttattca ttcataccac gctatcatgc ctaccgaact tcaaaagaa     480 agagaactca ccaagttcaa cccaaaggag ttgaactact tcttggaagg ttcccaagaa    540
agatccgaga tcatcagcaa catggtcgaa caaatgcaaa aagaccctat cttgaaggtc    600
gacgcttcat actacaactt gaccaaagac caacaaagag aagtcaccgc caagaagatt    660
gccagactct ccagatactt tgagcacgag tacccagacc aacaggccca gagattgtcg    720
atcctcggtg tctttgaccc acaagtcttc accagaatcg tgtcaacttg ggtttgttt     780 gtttcctgtg tccgtggtaa cggtaccaac tcccagttct tctactggac cataaataag    840
ggtatcgaca agttgagagg tatctatggt tgttttggta tgactgagtt ggcccacggt    900
tccaacgtcc aaggtattga accaccgcc acttttgacg aagacactga cgagtttgtc    960
atcaacaccc cacacattgg tgccaccaag tggtggatcg gtggtgctgc gcactccgcc    1020
acccactgct ccgtctacgc cagattgaag gtcaaaggaa aggactacgg tgtcaagacc    1080
tttgttgtcc cattgagaga ctccaaccac gacctcgagc caggtgtgac tgttggtgac    1140
attggtgcca agatgggtag agacggtatc gataacggtt ggatccagtt ctccaacgtc    1200
agaatcccaa gattctttat gttgcaaaag tactgtaagg tttcccgtct gggtgaagtc    1260
accatgccac catctgaaca attgtcttac tcggctttga ttggtggtag agtcaccatg    1320
atgatggact cctacagaat gaccagtaga ttcatcacca ttgccttgag atacgccatc    1380
cacagaagac aattcaagaa gaaggacacc gataccattg aaaccaagtt gattgactac    1440
ccattgcatc aaaagagatt gttcccattc ttggctgccg cttacttgtt ctcccaaggt    1500
gccttgtact tagaacaaac catgaacgca accaacgaca gttggacga agctgtcagt    1560 gctggtgaaa aggaagccat tgacgctgcc attgtcgaat ccaagaaatt gttcgtcgct    1620
tccggttgtt tgaagtccac ctgtacctgg ttgactgctg aagccattga cgaagctcgt    1680
caagcttgtg gtggtcacgg ttactcgtct tacaacggtt tcggtaaagc ctactccgac    1740
tgggttgtcc aatgtacctg ggaaggtgac aacaacatct tggccatgaa cgttgccaag    1800
ccaatggtta gagacttgtt gaaggagcca gaacaaaagg gattggttct ctccagcgtt    1860
gccgacttgg acgacccagc caagttggtt aaggctttcg accacgccct ttccggcttg    1920
gccagagaca ttggtgctgt tgctgaagac aaggggtttcg acattaccgg tccaagtttg    1980
gttttggttt ccaagttgaa cgctcacaga ttcttgattg acggtttctt caagcgtatc    2040
accccagaat ggtctgaagt cttgagacct ttgggtttct tgtatgccga ctggatcttg    2100
accaactttg gtgccacctt cttgcagtac ggtatcatta ccccagatgt cagcagaaag    2160
atttcctccg agcacttccc agccttgtgt gccaaggtta gaccaaacgt tgttggtttg    2220
actgatggtt tcaacttgac tgacatgatg accaatgctg ctattggtag atatgatggt    2280
aacgtctacg aacactactt cgaaactgtc aaggctttga acccaccaga aaacaccaag    2340
gctccatact ccaaggcttt ggaagacatg ttgaaccgtc cagaccttga agtcagagaa    2400
agaggtgaaa agtccgaaga agctgctgaa atccttgtcca gttaatagag cactaggttt    2460
tgataaattg gttcttacag tttatgtatt ttgattcttc cttttttaga tactttttt    2520
```

```
tatattttat tattccttat tgatgtaacg acagtcccac tataattaac ttaaactttg    2580
ctgtaaatca gatgacaagt gtttccctgt ttgcagggga gctc                    2624
```

<210> SEQ ID NO 25
<211> LENGTH: 456
<212> TYPE: DNA
<213> ORGANISM: Candida tropicalis

<400> SEQUENCE: 25

```
gaattcacat ggctaatttg gcctcggttc cacaacgcac tcagcattaa aaaaaaaata     60
cgcaatggca gctcggtcga cgcagcagaa gcgccgacgt accgtcgcgt tgccccgccc    120
atgcctcgcc gaccccctcca ccgccatcgt ttgcccattg tttgtggtag tgcgccgtga   180
cacaaaaact tgtcctgtca catgctgaag ttacaccaac ataactacta tgggattacg    240
taatcaaaaa tttcacagtt ttaacaaaaa aaaatcata caatcaacat tgggacatct     300
tgccctcccc cacaaaactt gcttctgcat caatcatata taaacatcat gaaataagcc    360
taaactcact tctttttttt tcatccttcc tacttcttct ttcatagtaa ctactttttt    420
tttattacca cacttattca ttcataccac gctatc                              456
```

<210> SEQ ID NO 26
<211> LENGTH: 455
<212> TYPE: DNA
<213> ORGANISM: Artificial Sequence
<220> FEATURE:
<223> OTHER INFORMATION: mutated POX promoter

<400> SEQUENCE: 26

```
gaattcacat ggctaatttg gcctcggttc cacaacgcac tcagcattaa aaaaaaaata     60
cgcaatggca gctcggtcga cgcagcagaa gcgccgacgt accgtcgcgt tgccccgccc    120
atgcctcgcc gaccccctcca ccgccatcgt ttgcccattg tttgtggtag tgcgccgtga   180
cacaaaaact tgtcctgtca catgctgaag ttacaccaac ataactacta tgggattacg    240
taatcaaaaa tttcacagtt ttaacaaaaa aaaatcatac aatcaacatt gggacatctt    300
gccctccccc acaaaacttg cttctgcatc aatcatatat aaacatcatg aaataagcct    360
aaactcactt ctttttttttt catccttcct acttcttctt tcatagtaac tactttttttt  420 ttattaccac acttattcat tcataccacg ctatc                               455
```

<210> SEQ ID NO 27
<211> LENGTH: 2623
<212> TYPE: DNA
<213> ORGANISM: Artificial Sequence
<220> FEATURE:
<223> OTHER INFORMATION: mutated POX gene

<400> SEQUENCE: 27

```
gaattcacat ggctaatttg gcctcggttc cacaacgcac tcagcattaa aaaaaaaata     60
cgcaatggca gctcggtcga cgcagcagaa gcgccgacgt accgtcgcgt tgccccgccc    120
atgcctcgcc gaccccctcca ccgccatcgt ttgcccattg tttgtggtag tgcgccgtga   180
cacaaaaact tgtcctgtca catgctgaag ttacaccaac ataactacta tgggattacg    240
taatcaaaaa tttcacagtt ttaacaaaaa aaaatcatac aatcaacatt gggacatctt    300
gccctccccc acaaaacttg cttctgcatc aatcatatat aaacatcatg aaataagcct    360
aaactcactt ctttttttttt catccttcct acttcttctt tcatagtaac tactttttttt  420 ttattaccac acttattcat tcataccacg ctatcatgcc taccgaactt caaaaagaaa    480
```

-continued

| | |
|---|---|
| gagaactcac caagttcaac ccaaaggagt tgaactactt cttggaaggt tcccaagaaa | 540 |
| gatccgagat catcagcaac atggtcgaac aaatgcaaaa agaccctatc ttgaaggtcg | 600 |
| acgcttcata ctacaacttg accaaagacc aacaaagaga agtcaccgcc aagaagattg | 660 |
| ccagactctc cagatacttt gagcacgagt acccagacca caggcccag agattgtcga | 720 |
| tcctcggtgt ctttgaccca caagtcttca ccagaatcgg tgtcaacttg ggtttgtttg | 780 |
| tttcctgtgt ccgtggtaac ggtaccaact cccagttctt ctactggacc ataaataagg | 840 |
| gtatcgacaa gttgagaggt atctatggtt gttttggtat gactgagttg gcccacggtt | 900 |
| ccaacgtcca aggtattgaa accaccgcca cttttgacga agacactgac gagtttgtca | 960 |
| tcaacacccc acacattggt gccaccaagt ggtggatcgg tggtgctgcg cactccgcca | 1020 |
| cccactgctc cgtctacgcc agattgaagg tcaaaggaaa ggactacggt gtcaagacct | 1080 |
| tgttgtccc attgagagac tccaaccacg acctcgagcc aggtgtgact gttggtgaca | 1140 |
| ttggtgccaa gatgggtaga gacggtatcg ataacggttg gatccagttc tccaacgtca | 1200 |
| gaatcccaag attctttatg ttgcaaaagt actgtaaggt ttcccgtctg ggtgaagtca | 1260 |
| ccatgccacc atctgaacaa ttgtcttact cggctttgat tggtggtaga gtcaccatga | 1320 |
| tgatggactc ctacagaatg accagtagat tcatcaccat tgccttgaga tacgccatcc | 1380 |
| acagaagaca attcaagaag aaggacaccg ataccattga aaccaagttg attgactacc | 1440 |
| cattgcatca aaagagattg ttcccattct tggctgccgc ttacttgttc tcccaaggtg | 1500 |
| ccttgtactt agaacaaacc atgaacgcaa ccaacgacaa gttggacgaa gctgtcagtg | 1560 |
| ctggtgaaaa ggaagccatt gacgctgcca ttgtcgaatc caagaaattg ttcgtcgctt | 1620 |
| ccggttgttt gaagtccacc tgtacctggt tgactgctga agccattgac gaagctcgtc | 1680 |
| aagcttgtgg tggtcacggt tactcgtctt acaacggttt cggtaaagcc tactccgact | 1740 |
| gggttgtcca atgtacctgg gaaggtgaca caaacatctt ggccatgaac gttgccaagc | 1800 |
| caatggttag agacttgttg aaggagccag aacaaaaggg attggttctc tccagcgttg | 1860 |
| ccgacttgga cgacccagcc aagttggtta aggctttcga ccacgcccct tccggcttgg | 1920 |
| ccagagacat tggtgctgtt gctgaagaca agggtttcga cattaccggt ccaagtttgg | 1980 |
| ttttggtttc caagttgaac gctcacagat tcttgattga cggtttcttc aagcgtatca | 2040 |
| ccccagaatg gtctgaagtc ttgagacctt gggtttctt gtatgccgac tggatcttga | 2100 |
| ccaactttgg tgccaccttc ttgcagtacg gtatcattac cccagatgtc agcagaaaga | 2160 |
| tttcctccga gcacttccca gccttgtgtg ccaaggttag accaaacgtt gttggtttga | 2220 |
| ctgatggttt caacttgact gacatgatga ccaatgctgc tattggtaga tatgatggta | 2280 |
| acgtctacga acactacttc gaaactgtca aggctttgaa cccaccagaa aacaccaagg | 2340 |
| ctccatactc caaggctttg gaagacatgt tgaaccgtcc agaccttgaa gtcagagaaa | 2400 |
| gaggtgaaaa gtccgaagaa gctgctgaaa tcttgtccag ttaatagagc actaggtttt | 2460 |
| gataatttgg ttcttacagt ttatgtattt tgattcttcc tttttagat acttttttt | 2520 |
| atatttatt attccttatt gatgtaacga cagtcccact ataattaact taaactttgc | 2580 |
| tgtaaatcag atgacaagtg tttccctgtt tgcaggggag ctc | 2623 |

<210> SEQ ID NO 28
<211> LENGTH: 2713
<212> TYPE: DNA
<213> ORGANISM: Candida tropicalis -continued

```
<400> SEQUENCE: 28
gtgatttggc acttgacagc gcgagagtgg ttaacacctg gtttccctca tttgggttct      60
gacatttgat aagttgaaag aacaatgcag aattcacatg gctaatttgg cctcggttcc     120
acaacgcact cagcattaaa aaaaaaatac gcaatggcag ctcggtcgac gcagcagaag     180
cgccgacgta ccgtcgcgtt gccccgccca tgcctcgccg acccctccac cgccatcgtt     240
tgcccattgt ttgtggtagt gcgccgtgac acaaaaactt gtcctgtcac atgctgaagt     300
tacaccaaca taactactat gggattacgt aatcaaaaat ttcacagttt taacaaaaaa     360
aaaatcatac aatcaacatt gggacatctt gccctccccc acaaaacttg cttctgcatc     420
aatcatatat aaacatcatg aaataagcct aaactcactt cttttttttt catccttcct     480
acttcttctt tcatagtaac tactttttt ttattaccac acttattcat tcataccacg     540
ctatcatgcc taccgaactt caaaagaaa gagaactcac caagttcaac ccaaaggagt     600
tgaactactt cttggaaggt tcccaagaaa gatccgagat catcagcaac atggtcgaac     660
aaatgcaaaa agaccctatc ttgaaggtcg acgcttcata ctacaacttg accaaagacc     720
aacaaagaga agtcaccgcc aagaagattg ccagactctc cagatacttt gagcacgagt     780
acccagacca acaggcccag agattgtcga tcctcggtgt ctttgaccca caagtcttca     840
ccagaatcgg tgtcaacttg ggtttgtttg tttcctgtgt ccgtggtaac ggtaccaact     900
cccagttctt ctactggacc ataaataagg gtatcgacaa gttgagaggt atctatggtt     960
gttttggtat gactgagttg gcccacggtt ccaacgtcca aggtattgaa accaccgcca    1020
cttttgacga agacactgac gagtttgtca tcaacaccc acacattggt gccaccaagt    1080
ggtggatcgg tggtgctgcg cactccgcca cccactgctc cgtctacgcc agattgaagg    1140
tcaaaggaaa ggactacggt gtcaagacct tgttgtccc attgagagac tccaaccacg    1200
acctcgagcc aggtgtgact gttggtgaca ttggtgccaa gatgggtaga gacggtatcg    1260
ataacggttg gatccagttc tccaacgtca gaatcccaag attctttatg ttgcaaaagt    1320
actgtaaggt ttcccgtctg ggtgaagtca ccatgccacc atctgaacaa ttgtcttact    1380 cggcttttgat tggtggtaga gtcaccatga tgatggactc ctacagaatg accagtagat    1440
tcatcaccat tgccttgaga tacgccatcc acagaagaca attcaagaag aaggacaccg    1500
ataccattga aaccaagttg attgactacc cattgcatca aaagagattg ttcccattct    1560
tggctgccgc ttacttgttc tcccaaggtg ccttgtactt agaacaaacc atgaacgcaa    1620
ccaacgacaa gttggacgaa gctgtcagtg ctggtgaaaa ggaagccatt gacgctgcca    1680
ttgtcgaatc caagaaattg ttcgtcgctt ccggttgttt gaagtccacc tgtacctggt    1740
tgactgctga agccattgac gaagctcgtc aagcttgtgg tggtcacggt tactcgtctt    1800
acaacggttt cggtaaagcc tactccgact gggttgtcca atgtacctgg gaaggtgaca    1860
acaacatctt ggccatgaac gttgccaagc caatggttag agacttgttg aaggagccag    1920
aacaaaaggg attggttctc tccagcgttg ccgacttgga cgacccagcc aagttggtta    1980
aggctttcga ccacgcccct tccggcttgg ccagagacat tggtgctgtt gctgaagaca    2040
agggtttcga cattaccggt ccaagtttgg ttttggtttc caagttgaac gctcacagat    2100
tcttgattga cggtttcttc aagcgtatca ccccagaatg gtctgaagtc ttgagacctt    2160
tgggtttctt gtatgccgac tggatcttga ccaactttgg tgccaccttc ttgcagtacg    2220
gtatcattac cccagatgtc agcagaaaga tttcctccga gcacttccca gccttgtgtg    2280
ccaaggttag accaaacgtt gttggtttga ctgatggttt caacttgact gacatgatga    2340
```

-continued

```
ccaatgctgc tattggtaga tatgatggta acgtctacga acactacttc gaaactgtca    2400
aggctttgaa cccaccagaa acaccaagg ctccatactc caaggctttg aagacatgt      2460 tgaaccgtcc agaccttgaa gtcagagaaa gaggtgaaaa gtccgaagaa gctgctgaaa    2520
tcttgtccag ttaatagagc actaggtttt gataatttgg ttcttacagt ttatgtattt    2580
tgattcttcc ttttttagat actttttttt atattttatt attccttatt gatgtaacga    2640
cagtcccact ataattaact taaactttgc tgtaaatcag atgacaagtg tttccctgtt    2700
tgcaggggag ctc                                                       2713

<210> SEQ ID NO 29
<211> LENGTH: 2712
<212> TYPE: DNA
<213> ORGANISM: Artificial Sequence
<220> FEATURE:
<223> OTHER INFORMATION: mutant POX gene

<400> SEQUENCE: 29
gtgatttggc acttgacagc gcgagagtgg ttaacacctg gtttccctca tttgggttct      60
gacatttgat aagttgaaag aacaatgcag aattcacatg gctaatttgg cctcggttcc     120
acaacgcact cagcattaaa aaaaaaatac gcaatggcag ctcggtcgac gcagcagaag     180
cgccgacgta ccgtcgcgtt gccccgccca tgcctcgccg accccctccac cgccatcgtt     240 tgcccattgt ttgtggtagt gcgccgtgac acaaaaactt gtcctgtcac atgctgaagt     300
tacaccaaca taactactat gggattacgt aatcaaaaat ttcacagttt taacaaaaaa     360
aaatcataca atcaacattg ggacatcttg ccctccccca caaaacttgc ttctgcatca     420
atcatatata aacatcatga ataagccta aactcacttc ttttttttc atccttccta      480 cttcttcttt catagtaact actttttttt tattaccaca cttattcatt catccacgc     540 tatcatgcct accgaacttc aaaagaaag agaactcacc aagttcaacc caaggagtt      600 gaactacttc ttggaaggtt cccaagaaag atccgagatc atcagcaaca tggtcgaaca    660
aatgcaaaaa gaccctatct tgaaggtcga cgcttcatac tacaacttga ccaaagacca     720
acaaagagaa gtcaccgcca agaagattgc cagactctcc agatactttg agcacgagta     780
cccagaccaa caggcccaga gattgtcgat cctcggtgtc tttgacccac aagtcttcac     840
cagaatcggt gtcaacttgg gttttgtttgt tcctgtgtc cgtggtaacg gtaccaactc    900
ccagttcttc tactggacca taaataaggg tatcgacaag ttgagaggta tctatggttg     960 tttggtatg actgagttgg cccacggttc aacgtccaa ggtattgaaa ccaccgccac    1020
ttttgacgaa gacactgacg agtttgtcat caacacccca cacattggtg ccaccaagtg    1080
gtggatcggt ggtgctgcgc actccgccac ccactgctcc gtctacgcca gattgaaggt    1140
caaaggaaag gactacggtg tcaagacctt tgttgtccca ttgagagact ccaaccacga    1200
cctcgagcca ggtgtgactg ttggtgacat tggtgccaag atgggtagag acggtatcga    1260
taacggttgg atccagttct ccaacgtcag aatcccaaga ttctttatgt tgcaaaagta    1320
ctgtaaggtt tcccgtctgg gtgaagtcac catgccacca tctgaacaat tgtcttactc    1380
ggctttgatt ggtggtagag tcaccatgat gatggactcc tacagaatga ccagtagatt    1440
catcaccatt gccttgagat acgccatcca cagaagacaa ttcaagaaga aggacaccga    1500
taccattgaa accaagttga ttgactaccc attgcatcaa aagagattgt tcccattctt    1560
ggctgccgct tacttgttct cccaaggtgc cttgtactta gaacaaacca tgaacgcaac    1620
caacgacaag ttggacgaag ctgtcagtgc tggtgaaaag gaagccattg acgctgccat    1680
```

-continued

```
tgtcgaatcc aagaaattgt tcgtcgcttc cggttgtttg aagtccacct gtacctggtt   1740
gactgctgaa gccattgacg aagctcgtca agcttgtggt ggtcacggtt actcgtctta   1800
caacggtttc ggtaaagcct actccgactg ggttgtccaa tgtacctggg aaggtgacaa   1860
caacatcttg gccatgaacg ttgccaagcc aatggttaga gacttgttga aggagccaga   1920
acaaaaggga ttggttctct ccagcgttgc cgacttggac gacccagcca agttggttaa   1980
ggctttcgac cacgcccttt ccggcttggc cagagacatt ggtgctgttg ctgaagacaa   2040
gggtttcgac attaccggtc caagtttggt tttggtttcc aagttgaacg ctcacagatt   2100
cttgattgac ggtttcttca agcgtatcac cccagaatgg tctgaagtct tgagaccttt   2160
gggtttcttg tatgccgact ggatcttgac caactttggt gccaccttct tgcagtacgg   2220
tatcattacc ccagatgtca gcagaaagat ttcctccgag cacttcccag ccttgtgtgc   2280
caaggttaga ccaaacgttg ttggtttgac tgatggtttc aacttgactg acatgatgac   2340
caatgctgct attggtagat atgatggtaa cgtctacgaa cactacttcg aaactgtcaa   2400
ggctttgaac ccaccagaaa acaccaaggc tccatactcc aaggctttgg aagacatgtt   2460
gaaccgtcca gaccttgaag tcagagaaag aggtgaaaag tccgaagaag ctgctgaaat   2520
cttgtccagt taatagagca ctaggttttg ataatttggt tcttacagtt tatgtatttt   2580
gattcttcct tttttagata cttttttttta tattttatta ttccttattg atgtaacgac   2640
agtcccacta taattaactt aaactttgct gtaaatcaga tgacaagtgt ttccctgttt   2700
gcaggggagc tc                                                       2712
```